(12) United States Patent
Elster et al.

(10) Patent No.: US 11,344,041 B2
(45) Date of Patent: May 31, 2022

(54) HUMAN MILK PRODUCTS USEFUL IN PRE- AND POST-OPERATIVE CARE

(71) Applicant: Prolacta Bioscience, Inc., City of Industry, CA (US)

(72) Inventors: Scott Elster, City of Industry, CA (US); Joseph Fournell, City of Industry, CA (US)

(73) Assignee: PROLACTA BIOSCIENCE, INC., City of Industry, CA (US)

(*) Notice: Subject to any disclaimer, the term of this patent is extended or adjusted under 35 U.S.C. 154(b) by 565 days.

(21) Appl. No.: 16/067,241

(22) PCT Filed: Dec. 29, 2016

(86) PCT No.: PCT/US2016/069250
§ 371 (c)(1),
(2) Date: Jun. 29, 2018

(87) PCT Pub. No.: WO2017/117409
PCT Pub. Date: Jul. 6, 2017

(65) Prior Publication Data
US 2019/0021357 A1 Jan. 24, 2019

Related U.S. Application Data

(60) Provisional application No. 62/273,243, filed on Dec. 30, 2015.

(51) Int. Cl.
| | |
|---|---|
| *A23C 9/20* | (2006.01) |
| *A23L 33/00* | (2016.01) |
| *A61K 38/01* | (2006.01) |
| *A23L 33/19* | (2016.01) |
| *A23C 3/02* | (2006.01) |
| *A23C 9/142* | (2006.01) |

(52) U.S. Cl.
CPC .............. *A23C 9/206* (2013.01); *A23L 33/40* (2016.08); *A61K 38/018* (2013.01); *A23C 3/02* (2013.01); *A23C 9/1422* (2013.01); *A23L 33/19* (2016.08)

(58) Field of Classification Search
CPC ......... A23C 9/206; A23C 3/02; A23C 9/1422; A23L 2/52; A23L 2/66; A23L 33/10; A23L 33/15; A23L 33/16; A23L 33/19; A23L 33/40; C12Q 1/6809; A61K 38/018
See application file for complete search history.

(56) References Cited

U.S. PATENT DOCUMENTS

| | | |
|---|---|---|
| 2,567,898 A | 9/1951 | Staaff |
| 3,946,113 A | 3/1976 | Seiberling |
| 4,362,697 A | 12/1982 | Tabb et al. |
| 4,455,483 A | 6/1984 | Schonhuber |
| 4,762,822 A | 8/1988 | Ettinger |
| 4,772,262 A | 9/1988 | Grant et al. |
| 4,876,100 A | 10/1989 | Holm et al. |
| 4,948,599 A | 8/1990 | Sagara et al. |
| 5,064,674 A | 11/1991 | Girsh |
| 5,169,766 A | 12/1992 | Schuster et al. |
| 5,256,437 A | 10/1993 | Degen et al. |
| 5,303,598 A | 4/1994 | Binder |
| 5,334,822 A | 8/1994 | Sanford |
| 5,340,603 A | 8/1994 | Neylan et al. |
| 5,401,523 A | 3/1995 | Degen et al. |
| 5,492,938 A | 2/1996 | Kyle et al. |
| 5,505,955 A | 4/1996 | Petersen et al. |
| 5,541,065 A | 7/1996 | Erlich et al. |
| 5,576,040 A | 11/1996 | Moller et al. |
| 5,605,689 A | 2/1997 | Ammann |
| 5,616,483 A | 4/1997 | Bjursell et al. |
| 5,670,196 A | 9/1997 | Gregory |
| 5,683,733 A | 11/1997 | Krabsen et al. |
| 5,707,678 A | 1/1998 | Gregory |
| 5,972,337 A | 10/1999 | Ceriani et al. |
| 5,983,198 A | 11/1999 | Mowery |
| 6,004,288 A | 12/1999 | Hochstedler et al. |
| 6,017,511 A | 1/2000 | Wong et al. |
| 6,020,015 A | 2/2000 | Gaull |
| 6,056,978 A | 5/2000 | Beck et al. |
| 6,183,803 B1 | 2/2001 | Morcol et al. |
| 6,194,009 B1 | 2/2001 | Kamerel |
| 6,270,827 B1 | 8/2001 | Gaull et al. |
| 6,294,206 B1 | 9/2001 | Barrett-Reis et al. |
| 6,426,109 B1 | 7/2002 | Ehsani et al. |
| 6,613,367 B1 | 9/2003 | Wells et al. |

(Continued)

FOREIGN PATENT DOCUMENTS

| | | |
|---|---|---|
| CN | 101873806 A | 10/2010 |
| CN | 102511557 A | 6/2012 |

(Continued)

OTHER PUBLICATIONS

[Author Unknown] "Incidence and Prevalence", Advanced Renal Education (2012); pp. 1-2, advancedrenaleducation.com/content/incidence-and-prevalence.

[Author Unknown], Nutrients Unit Preterm Human Milk Alone Prolact +4 Preterm Human Milk Fortified With (Prolacta+4 H2MF® Nutrition Information; Prolact+6 H2MF® Nutrition Information, Prolact+8 H2MF® Nutrition Information; and Prolact+10 H2MF® Nutrition Information), Jan. 1, 2014 (Jan. 1, 2014), pp. 1-4, XP055710450, Retrieved from the Internet: URL:http://web.archive.org/web/20150909231449if_/http://www.prolacta.com/Data/Sites/14/media/PDF/mkt-180-prolact-hmf-nutritionlabels.pdf [retrieved on Jul. 1, 2020].

Arslanoglu, et al., "Optimization of human milk fortification for preterm infants: new concepts and recommendations". J Perinat Med. (May 2010); 38(3): 233-238.

(Continued)

*Primary Examiner* — Aaron J Kosar
(74) *Attorney, Agent, or Firm* — Medler Ferro Woodhouse & Mills PLLC

(57) ABSTRACT

The present disclosure relates to human milk compositions and methods of making and using the same. In particular, the disclosure features methods of using human milk compositions to feed subjects before and/or after surgery or medical operations and that are useful in promoting recovery.

13 Claims, 5 Drawing Sheets

(56) References Cited

U.S. PATENT DOCUMENTS

| | | |
|---|---|---|
| 6,635,296 B1 | 10/2003 | Nissen et al. |
| 6,652,900 B2 | 11/2003 | Lindquist |
| 6,670,124 B1 | 12/2003 | Chow et al. |
| 6,737,096 B2 | 5/2004 | Lindquist |
| 6,780,987 B1 | 8/2004 | Herman et al. |
| 6,846,298 B1 | 1/2005 | Carr et al. |
| 6,910,594 B2 | 6/2005 | Foley et al. |
| 7,867,541 B2 | 1/2011 | McMahon et al. |
| 7,914,822 B2 | 3/2011 | Medo |
| 7,943,315 B2 | 5/2011 | Medo et al. |
| 7,951,410 B2 | 5/2011 | McMahon et al. |
| 8,278,046 B2 | 10/2012 | Medo et al. |
| 8,377,445 B2 | 2/2013 | Medo et al. |
| 8,545,920 B2 | 10/2013 | Medo et al. |
| 8,628,921 B2 | 1/2014 | Medo et al. |
| 8,821,878 B2 | 9/2014 | Medo et al. |
| 9,149,052 B2 | 10/2015 | Medo et al. |
| 11,122,813 B2 | 9/2021 | Elster et al. |
| 2001/0034614 A1 | 10/2001 | Fletcher-Haynes et al. |
| 2001/0049096 A1 | 12/2001 | Brown |
| 2002/0155445 A1 | 10/2002 | Jarvi |
| 2002/0182243 A1 | 12/2002 | Medo |
| 2003/0093171 A1 | 5/2003 | Soehnlen |
| 2003/0152942 A1 | 8/2003 | Fors et al. |
| 2003/0175701 A1 | 9/2003 | Griffiths et al. |
| 2003/0219812 A1 | 11/2003 | Quay et al. |
| 2004/0181205 A1 | 9/2004 | Morton et al. |
| 2004/0265462 A1 | 12/2004 | Carlson |
| 2005/0053707 A1 | 3/2005 | Kopf et al. |
| 2005/0096295 A1 | 5/2005 | McMahon et al. |
| 2005/0100634 A1 | 5/2005 | Medo |
| 2005/0214358 A1 | 9/2005 | Mikoshiba et al. |
| 2005/0220894 A1 | 10/2005 | Williams et al. |
| 2006/0115558 A1 | 6/2006 | Lamothe |
| 2006/0204632 A1 | 9/2006 | Barrett Reis et al. |
| 2006/0233915 A1 | 10/2006 | Puski et al. |
| 2007/0098863 A1 | 5/2007 | Medo et al. |
| 2007/0104700 A1 | 5/2007 | Garcia-Rodenas et al. |
| 2007/0203802 A1 | 8/2007 | Medo et al. |
| 2008/0118615 A1 | 5/2008 | Hartmann et al. |
| 2008/0124430 A1 | 5/2008 | Medo et al. |
| 2008/0187619 A1 | 8/2008 | Hartmann et al. |
| 2008/0227101 A1 | 9/2008 | Medo et al. |
| 2008/0254165 A1 | 10/2008 | Patel et al. |
| 2008/0274230 A1 | 11/2008 | Johns et al. |
| 2009/0181848 A1 | 7/2009 | Lenz et al. |
| 2009/0203592 A1 | 8/2009 | Beermann et al. |
| 2009/0258121 A1 | 10/2009 | Medo |
| 2010/0268658 A1 | 10/2010 | Medo et al. |
| 2010/0280115 A1 | 11/2010 | Medo et al. |
| 2011/0206684 A1 | 8/2011 | Medo |
| 2011/0256233 A1 | 10/2011 | Fournell et al. |
| 2011/0256269 A1 | 10/2011 | Medo et al. |
| 2011/0311689 A1 | 12/2011 | Medo et al. |
| 2012/0171165 A1 | 7/2012 | Buck et al. |
| 2012/0238626 A1 | 9/2012 | Gibson et al. |
| 2013/0059050 A1 | 3/2013 | Fournell et al. |
| 2013/0059815 A1 | 3/2013 | Fournell et al. |
| 2013/0195989 A1 | 8/2013 | Medo et al. |
| 2014/0037787 A1 | 2/2014 | Haschke et al. |
| 2014/0271980 A1 | 9/2014 | Eaker et al. |
| 2014/0272027 A1 | 9/2014 | Elster et al. |
| 2017/0367364 A1 | 12/2017 | Lee et al. |
| 2018/0104279 A1 | 4/2018 | Elster et al. |
| 2019/0327993 A1 | 10/2019 | Elster et al. |
| 2021/0106626 A1* | 4/2021 | Ma .................. A23L 33/19 |

FOREIGN PATENT DOCUMENTS

| | | | | |
|---|---|---|---|---|
| CN | 109714975 A | * | 5/2019 | ............. A61K 35/20 |
| EP | 0533552 A1 | | 3/1993 | |
| EP | 1637043 | | 3/2006 | |
| GB | 1451747 A | | 10/1976 | |
| JP | 61-33895 U | | 1/1986 | |
| JP | 64-67141 A | | 3/1989 | |
| JP | 6-303900 A | | 11/1994 | |
| JP | 2001-017078 A | | 1/2001 | |
| JP | 2002-068998 A | | 3/2002 | |
| JP | 2002068998 A | | 3/2002 | |
| JP | 2002-532074 A | | 10/2002 | |
| JP | 2002-540806 A | | 12/2002 | |
| JP | 2005-525116 A | | 8/2005 | |
| JP | 2010-502186 A | | 1/2010 | |
| JP | 2010-126495 A | | 6/2010 | |
| JP | 2011-504365 A | | 2/2011 | |
| JP | 2011-172569 A | | 9/2011 | |
| JP | 2012-254091 A | | 12/2012 | |
| SE | 380422 B | | 11/1975 | |
| WO | WO 1998/057549 A1 | | 12/1998 | |
| WO | WO 2000/043550 A2 | | 7/2000 | |
| WO | WO 2000/060949 A2 | | 10/2000 | |
| WO | WO 2005/013709 A1 | | 2/2005 | |
| WO | WO 2005/051088 A2 | | 6/2005 | |
| WO | WO 2005/084129 A2 | | 9/2005 | |
| WO | WO 2006/026878 A1 | | 3/2006 | |
| WO | WO 2006/026879 A1 | | 3/2006 | |
| WO | WO 2007/035870 A2 | | 3/2007 | |
| WO | WO 2008/027572 A1 | | 3/2008 | |
| WO | WO 2008/067486 A2 | | 6/2008 | |
| WO | WO 2008/073888 A2 | | 6/2008 | |
| WO | WO 2008/119163 A1 | | 10/2008 | |
| WO | WO 2009/068549 A1 | | 6/2009 | |
| WO | WO 2010/030764 A2 | | 3/2010 | |
| WO | WO 2011/144221 A1 | | 11/2011 | |
| WO | WO 2012/030764 A2 | | 3/2012 | |
| WO | WO 2014/158907 A1 | | 10/2014 | |
| WO | WO 2014/158911 A1 | | 10/2014 | |
| WO | WO 2016/109659 A1 | | 7/2016 | |
| WO | WO 2016/168698 A1 | | 10/2016 | |
| WO | WO 2017/117409 A1 | | 7/2017 | |

OTHER PUBLICATIONS

Embleton, Nicholas D., "Nutrition following surgery in the preterm infant", Sep. 11, 2014 (Sep. 11, 2014), XP055624216, Retrieved from the Internet: URL:http://www.infantjournal.co.uk/pdf/inf_059_low.pdf [retrieved on Sep. 19, 2019], 4 pages.

Ghandehari, et al., "An exclusive human milk-based diet in extremely premature infants reduces the probability of remaining on total parenteral nutrition: a reanalysis of the data". BMC Res Notes (Apr. 25, 2012); 5: 188.

Gianni, et al., "The role of nutrition in promoting growth in pre-term infants with bronchopulmonary dysplasia: a prospective non-randomised interventional cohort study". BMC Pediatr. (Sep. 22, 2014); 14: 235, pp. 1-6.

Hair, Amy B., "Innovations in Human Milk: Putting Evidence to Practice" Aug. 15, 2011 (Aug. 15, 2011), pp. 1-49, XP055617580, Retrieved from the Internet: URL:http://www.nicuniversity.org/Portals/1/Downloads/Prolacta_Sympo_Hair.pptx [retrieved on Sep. 2, 2019].

Kim, et al., "Growth and Tolerance of Preterm Infants Fed a New Extensively Hydrolyzed Liquid Human Milk Fortifier". J Pediatr Gastroenterol Nutr. (Dec. 2015); 61(6): 665-671.

Liu, et al., "Human milk fortifier with high versus standard protein content for promoting growth of preterm infants: A meta-analysis". J Int Med Res. (Jun. 2015); 43(3): 279-289. Epub May 8, 2015.

Extended European Search Report for European Patent Application No. 16882669.1, dated Oct. 1, 2019, 23 pages.

Black, et al., "Incremental Hospital Costs Associated With Comorbidities of Prematurity". Managed Care Magazine Online (Dec. 2015); downloaded on Jan. 25, 2017 at https://www.managedcaremag.com/linkout/2015/12/54, 14 pages.

Bloom, B.T., "Safety of donor milk: a brief report". Journal of Perinatology (May 2016); 36(5): 392-393. Epub Jan. 7, 2016.

Ford, et al., "Improved feeding tolerance and growth are linked to increased gut microbial community diversity in very-low-birth-weight infants fed mother's own milk compared with donor breast milk". The American Journal of Clinical Nutrition (Apr. 1, 2019); 109(4): 1088-1097.

(56) References Cited

OTHER PUBLICATIONS

Ganapathy, "Long term healthcare costs of infants who survived neonatal necrotizing enterocolitis: a retrospective longitudinal study among infants enrolled in Texas Medicaid". BMC Pediatrics (Aug. 20, 2013); 13: 127, 11 pages.
Hair, Amy, "Human Milk as a Caloric Supplement in Pre-Term Infants", ClinicalTrials.gov Identifier NCT01487928, https://clinicaltrials.gov/ct2/show/study/NCT0487928?term=human+milk&cond=Premature&cntry=US&rank=5), First Posted Dec. 8, 2011, downloaded Jun. 21, 2019, 9 pages.
Hair, et al., "Beyond Necrotizing Enterocolitis Prevention: Improving Outcomes with an Exclusive Human Milk-Based Diet". Breastfeeding Medicine (Mar. 2016); 11(2): 70-74. Epub Jan. 20, 2016.
Hair, et al., "Beyond Necrotizing Enterocolitis: Other Clinical Advantages of an Exclusive Human Milk Diet". Breastfeeding Medicine (Jul./Aug. 2018); 13(6): 408-411. Epub Jun. 7, 2018.
Herrmann and Carroll, "An Exclusively Human Milk Diet Reduces Necrotizing Enterocolitis". Breastfeeding Medicine (May 1, 2014); 9(4): 184-190.
Hicks, et al., "Calcium Absorption in Very Low Birth Weight Infants with and without Bronchopulmonary Dysplasia". The Journal of Pediatrics (Jun. 2011); 158(6): 885-890.e1. Epub Feb. 6, 2011.
Huston, et al., "Decreasing Necrotizing Enterocolitis and Gastrointestinal Bleeding in the Neonatal Intensive Care Unit: The Role of Donor Human Milk and Exclusive Human Milk Diets in Infants >1500 g Birth Weight". ICAN: Infant, Child, & Adolescent Nutrition (Jan. 10, 2014); 6(2): 86-93.
Huston, et al., "Improving Growth for Infants ≤1250 Grams Receiving an Exclusive Human Milk Diet". Nutrition in Clinical Practice (Oct. 2018); 33(5): 671-678. Epub Feb. 16, 2018.
Khandelwal, et al., "A Pilot Study of Human Milk to Reduce Intestinal Inflammation After Bone Marrow Transplant". Breastfeeding Medicine (Apr. 2019); 14(3):193-202. Epub Mar. 27, 2019.
Kornhauser and Schneiderman, "How Plans Can Improve Outcomes and Cut Costs for Preterm Infant Care." Managed Care (Jan. 2010); 19(1): 28-30.
Lucas and Cole, "Medical Science". The Lancet (1980); 336(8730-8731): 1519-1523.
Lucas, et al., "Breast milk and subsequent intelligence quotient in children born preterm". The Lancet (Feb. 1, 1992); 339(8788): 261-264.
Lucas, et al., "Randomised trial of early diet in preterm babies and later intelligence quotient". BMJ (Nov. 28, 1998); 317(7171): 1481-1487.
Rechtman, et al., "Effect of Environmental Conditions on Unpasteurized Donor Human Milk". Breastfeeding Medicine (Spring 2006); 1(1): 24-26.
Reeves, et al., "TGF-β2, a Protective Intestinal Cytokine, Is Abundant in Maternal Human Milk and Human-Derived Fortifiers but Not in Donor Human Milk". Breastfeeding Medicine (Dec. 2013); 8(6): 496-502. Epub Jul. 19, 2013.
Sandhu, et al., "Human-Based Human Milk Fortifier as Rescue Therapy in Very Low Birth Weight Infants Demonstrating Intolerance to Bovine-Based Human Milk Fortifier". Breastfeeding Medicine (Nov. 2017); 12(9): 570-573. Epub Aug. 4, 2017.
Schanler, et al., "Randomized Trial of Donor Human Milk Versus Preterm Formula as Substitutes for Mothers' Own Milk in the Feeding of Extremely Premature Infants". Pediatrics (Aug. 2005); 116(2): 400-406.
Visuthranukul, C., et al., "Premature small for gestational age infants fed an exclusive human milk-based diet achieve catch-up growth without metabolic consequences at 2 years of age". Arch Dis Child Fetal Neonatal Ed. (May 2019); 104(3): F242-F247. Epub Nov. 13, 2018.
[Author Unknown], "CARE + WEAR What is TPN and How is it Administered?" Definition: Total Parenteral Nutrition (2018), downloaded Apr. 25, 2019 from https://www.careandwear.com/blogs/commun ity/124683651-what-is-tpn-and-how-is-it-administered, 5 pages.
[Author Unknown], "Neonatal Parenteral Nutrition", UCSF Children's Hospital, Intensive Care Nursery House Staff Manual, 2004-2006, The Regents of the University of California; pp. 136-142, 7 pages.
Jenq, et al., "Regulation of intestinal inflammation by microbiota following allogeneic bone marrow transplantation." J Exp Med. (May 7, 2012); 209(5): 903-911.
Partial Supplementary European Search Report for European Patent Application No. 16882669.1, dated May 31, 2019, 13 pages.
[Author Unknown] "Home parenteral nutrition". Mayo Clinic / Mayo Foundation for Medical Education and Research (MFMER) 1998-2019, pp. 1-3, downloaded Oct. 29, 2019, https://www.mayoclinic.org/tests-procedures/total-parenteral-nutrition/about/pac-20385081?p= 1.
Fuji, et al., "Systematic Nutritional Support in Allogeneic Hematopoietic Stem Cell Transplant Recipients". Biology of Blood and Marrow Transplantation (Oct. 2015); 21(10): 1707-1713. Epub Jul. 11, 2015.
Hair, Amy B., "Innovations in Human Milk: Putting Evidence to Practice" pp. 1-49, XP055617580, Retrieved from the Internet: URL:http://www.nicuniversity.org/Portals/1 /Downloads/Prolacta_Sympo_Hair.pptx [retrieved on Sep. 2, 2019], Hot Topics in Neonatology Conference, Dec. 6-9, 2015, Washington DC; slides available online on Jan. 13, 2016.
Wilson, et al., "Parenteral Nutrition Utilization in Bone Marrow Transplant Recipients". Journal of Nutrition and Health Sciences (May 20, 2014); vol. 1, Issue 1, pp. 1-4.
Xiao, et al., "Human Milk Oligosaccharide 2'-Fucosyllactose Improves Innate and Adaptive Immunity in an Influenza-Specific Murine Vaccination Model". Frontiers in Immunology (Mar. 9, 2018); 9:452. eCollection 2018.
"Breastfeeding and the use of human milk." American Academy of Pediatrics, Pediatrics (2012); 129(3): e827-e841.
[Author Unknown], Intermountain Healthcare, Pasteurized Human Milk, Fact Sheet for Patients and Families, 2010, pp. 1-2.
AAP Committee on Nutrition, AAP Section on Breastfeeding, AAP Committee on Fetus and Newborn. Donor Human Milk for the High-Risk Infant: Preparation, Safety, and Usage Options in the United States. Pediatrics (2017); 139 (1): e20163440, 8 pages.
Abrams, et al., "Greater Mortality and Morbidity in Extremely Preterm Infants Fed a Diet Containing Cow Milk Protein Products." Breastfeeding Medicine (2014); 9 (6): 281-285.
Anderson, et al., "Variation in Growth of Infants with a Single Ventricle." The Journal of Pediatrics (2012); 161 (1): 16-21. e3.
Aoyama, Kazutoshi, et al., "Improved outcome of allogeneic bone marrow transplantation due to breastfeeding-induced tolerance to maternal antigens." Blood (2009); 113.8: 1829-1833.
Arnold, "How North American Donor Banks Operate: Results of a Survey: Part 1," J. Hum. Lact. (1997); 13(2):159-162.
Arnold, "How North American Donor Banks Operate: Results of a Survey: Part 2," J. Hum. Lact. (1997); 13(3):243-246.
Arnold, "How to Order Banked Donor Milk in the United States: What the Health Care Provider Needs to Know," J. Hum. Lact. 14(1):65-67 (1998).
Arnold, Human Milk in the NICU. Policy Into Practice. (2010); pp. 3-11, pp. 15-46; pp. 191-207; pp. 311-367, 121 pages.
Atkinson, et al., "Special nutritional needs of infants for prevention of and recovery from bronchopulmonary dysplasia." J Nutr. (2001); 131(3): 942S-946S.
Baveja, et al., "Pharmacological strategies in the prevention and management of bronchopulmonary dysplasia." Semin Perinatol. (2006); 30(4): 209-218.
Bernshaw, N.J., "Milk Banking: an Idea That Has Come of Age. Non-Profit Milk Banking," Seminar delivered at Utah Breastfeeding Coalition Meeting, Aug. 29, 2006.
Biniwale, et al., "The role of nutrition in the prevention and management of bronchopulmonary dysplasia." Semin Perinatol. (2006); 30(4): 200-208.
Bode, Lars, and Jantscher-Krenn, Evelyn. "Structure-function relationships of human milk oligosaccharides." Advances in Nutrition: An International Review Journal (2012); 3.3: 383S-391S.
Boehm, G., et al., "Metabolic Differences Between AGA- and SGA-Infants of Very Low Birthrate II Relationship to Protein

(56) References Cited

OTHER PUBLICATIONS

Intake," Acta Paediatrics Scaninavica, Almquist, Och Wiksell, Stockholm, SE 77(5):642-646, Jan. 1, 1988.
Burger and Schumm, "Detection of a Minor contributor in a DNA Sample Mixture from Human Milk," International Congress Series, 1288:547-549 (2006).
Burger et al., "Detection of a 1% to 2% Contributor in a DNA Sample Mixture From Human Milk," International Society for Forensic Genetics 21st Congress Conference Programme and Abstracts [online], Sep. 12-17, 2005 [retrieved on Mar. 26, 2007]. Retrieved from the Internet: http://www.ipatimup.pt/isfg2005/PROGRAMME.pdf; p. 75.
Cabre et al., "Polyunsaturated Fatty Acid Deficiency in Liver Cirrhosis: Its Relation to Associated Protein-Energy Malnutrition (Preliminary Report).", American Journal of Gastroenterology, 83(7): 712-717 (1988). (Abstract).
Carey et al., "Growth and phosphorus metabolism in premature infants fed human milk, fortified human milk, or special premature formula. Use of serum procollagen as a marker of growth," Am. J. Dis. Children 141(5):511-515 (1987).
Casey, "The nutritive and metabolic advantages of homologous milk," Proc. Nutr. Soc. 48:271-281 (1989).
Cowan et al., "Milk permeate as a dietary supplement for lactating dairy cows," Aus. J. Exp. Agric. 30(6):807-810 (1990).
Coxson, et al., "Early emphysema in patients with anorexia nervosa." Am J Respir Crit Care Med. (2004); 170(7): 748-752.
Cristofalo et al. "Randomized trial of exclusive human milk versus preterm formula diets in extremely premature infants." Journal of Pediatrics (2013); 163.6: 1592-1595.
Database Medline [Online] US National Library of Medicine (NLM), Bethesda, MD, US; Jul. 1979 (Jul. 1979), Jenness R: "The composition of human milk." Database accession No. NLM392766, XP002785943, 2 pages.
Davies, D. P., "Adequacy of Expressed Breast Milk for Early Growth of Preterm Infants," Arch. Disease in Childhood. 1977. vol. 52, pp. 296-301.
Davies, Stella M., "A Pilot Study of Donor Enteral Human Milk to Modulate the Gut Microbiome in Children Receiving Stem Cell Transplant", 2015 BMT Tandem Meetings, Feb. 11, 2015, San Diego, CA, Poster Abstract—Copyright 2011, BMT Tandem, XP055518062, Retrieved from the Internet: URL:https://bmt.confex.com/tandem/2015/webprogram/Paper5173.html [retrieved on Oct. 23, 2018], 2 pages.
De Halleux, et al., "Variability in human milk composition: benefit of individualized fortification in very-low-birth-weight infants." Am J Clin Nutr. (2013); 98(2): 529S-35S.
Duckduckgosling: "Breastmilk Ice Cream!!", youtube, Apr. 11, 2012 (Apr. 11, 2012), p. 2 pp., XP054976962, Retrieved from the Internet: URL:www.youtube.com/watch?v=yMoJhJYvmYQ [retrieved on Dec. 1, 2016] * the whole document*.
Edmond and Bahl, "Optimal feeding of low-birth-weight infants." World Health Organization (2006); pp. 1-121, 131 pages.
Ehrenkranz, et al., "Early, aggressive nutritional management for very low birth weight infants: what is the evidence?." Semin Perinatol. (2007); 31(2): 48-55.
Ehrenkranz, et al., "Ongoing issues in the intensive care for the periviable infant-nutritional management and prevention of bronchopulmonary dysplasia and nosocomial infections." Semin Perinatol. (2014); 38(1): 25-30.
Extended European Search Report for European Patent Application No. 15876253.4, dated Oct. 25, 2018, 9 pages.
Extended European Search Report in EP Application No. EP 12188676.6 dated Feb. 27, 2013.
Extended European Search Report in EP Application No. EP 14774486.6 dated Dec. 9, 2016,10 pages.
Extended European Search Report in EP Application No. EP 16780903.7 dated Nov. 9, 2018, 9 pages.
Friis and Andersen, "Rate of inactivation of cytomegalovirus in raw banked milk during storage at −20° C. and pasteurisation," Br. Med. J. 285:1604-1605 (1982).
Fukushima et al., "Consumption of cow milk and egg by lactating women and the presence of β-lactoglobulin and ovalbumin in breast milk," Am. J. Clin. Nutr. 65:30-35 (1997).
Gartner et al., "Breastfeeding and the use of human milk," Pediatr. 115(2):496-506 (2005).
Geilman et al., "Production of an electrolyte beverage from milk permeate," J. Dairy Sci. 75(9):2364-2369 (1992).
Hagelberg S., et al., "Amino Acid Levels in the Critically Ill Preterm Infant Given Mother's Milk Fortified with Protein from Human or Cow's Milk" Acta Paediatr Scan. 1990. vol. 79, pp. 1163-1174.
Hagelberg, S., et al., "The Protein Tolerance of Very Low Birth Weight Infants Fed Human Milk Protein Enriched Mothers' Milk" Acta Paediatr Scan. 1982. vol. 71, pp. 597-601.
Hair et al., "Premature Infants 750-1,250 g Birth Weight Supplemented with a Novel Human Milk-Derived Cream are Discharged Sooner." Breastfeeding Medicine (2016); 11(3): 133-137.
Hair, et al., "Human milk feeding supports adequate growth in infants ≤ 1250 grams birth weight." BMC Research Notes (2013); 6: 459.
Hair, et al., "Randomized trial of human milk cream as a supplement to standard fortification of an exclusive human milk-based diet in infants 750-1250 g birth weight." J Pediatr. (2014); 165(5): 915-920.
Hartmann, B.T., et al. "Best Practice Guidelines for the Operation of a Donor Human Milk Bank in an Australian NICU," Early Human Devel. (2007); 83:667-673.
Hawthorne, et al., "Current issues in nutritional management of very low birth weight infants." Minerva Pediatr. (2004); 56(4): 359-372.
Heiman and Schanler, "Benefits of maternal and donor human milk for premature infants." Early Human Development (2006); 82 (12): 781-787.
Hylmo, P., et al., "Preparation of Fat and Protein from Banked Human Milk: Its Use in Feeding Very-Low-Birth-Weight Infants," Human Milk Banking, edited by A.F. Williams and J.D. Baum, Nestle Nutrition, Vewey/Raven Press, New York, 1984, pp. 55-61.
Itabashi et al., "Fortified preterm human milk for very low birth weight infants," Early Hum. Devel. (1992); 29:339-343.
Jacobs, et al., "An empirically based tool for analyzing morbidity associated with operations for congenital heart disease." The Journal of Thoracic and Cardiovascular Surgery (2013); 145 (4): 1046-1057. e1.
Jenness and Palmer, "Substances Adsorbed on the Fat Globules in Cream and Their Relation to Churning. V. Composition of the 'Membrane' and Distribution of the Adsorbed Substances in Churning," J. Dairy Science (1945); 28(8):611-623.
Jensen et al., "Lipids of Bovine and Human Milks: A Comparison," J. Dairy Science 73:223-40, 1990.
Jensen, R.G. et al., "Lipids in Human Milk and Infant Formulas," Annual Review of Nutrition (1992); 12:417-441.
Jiaxiang, Zhang, et al., People's Medical Publishing House, p. 181, Dec. 2006, with English translation, 4 pages.
Jobe, et al., "Let's feed the preterm lung." J Pediatr (Rio J) (2006); 82(3): 165-166.
Johnson, et al., "Cost of morbidities in very low birth weight infants." J Pediatr. (2013); 162(2): 243-249.e1.
Kim, et al., "Human Milk Banking." Paediatrics & Child Health (Nov. 2010); 15 (9): 595-598.
Klein, Catherine, J., "Nutrient Requirements for Preterm Infant Formulas 123," Life Sciences Research Office, J Nutr (2002); 132:1935S-1577S.
Krukovsky et al., "The Effects of Nordihydroguaiaretic Acid, Salt, and Temperature of Storage on the Stability of Fat and Fat-Soluble Vitamins in Cream and Butter," J. Dairy Science (1949); 32(7):679-687.
Kuschel and Harding, "Fat supplementation of human milk for promoting growth in preterm infants." Cochrane Database of Systematic Reviews (2007); Issue 4, Art. No. CD000341, DOI: 10.1002/14651858.CD000341.
Kuzma-O'Reilly, B., et al., "Evaluation, Development, and Implementation of Potentially Better Practices in Neonatal Intensive Care Nutrition." Pediatrics (2003); 111 (4): e461-e470, 12 pages.

(56) References Cited

OTHER PUBLICATIONS

Lake, Frank, "Breast Milk Ice Cream: Weekly World News", Feb. 25, 2011 (Feb. 25, 2011), XP055324916, Retrieved from the Internet: URL:http://weeklyworldnews.com/headlines/29979/breast-milk-ice-cream/[retrieved on Nov. 30, 2016] * the whole document*.
Lapillone, et al., "Mineral balance and whole body bone mineral content in very low-birth-weight infants", Acta Pediatrica (1994); 84 (s405):117-122.
Lawrence, "Storage of human milk and the influence of procedures on immunological components of human milk," Acta Pædiatr. (1999); 88:14-18.
Lindblad B.S., et al., "Blood Levels of Critical Amino Acids in Very Low Birthweight Infants on a High Human Milk Protein Intake" Acta Paediatr Scan. (1982); vol. 296, pp. 24-27.
Lönnerdal, "Biochemistry and physiological function of human milk proteins," Am. J. Clin. Nutr. 42:1299-1317 (1985).
Lucas, et al., "A human milk formula." Early Hum. Devel. (1980); 4 (1): 15-21.
Luck and Nau, "Nicotine and cotinine concentrations in the milk of smoking mothers: influence of cigarete consumption and diurnal variation," Eur J. Pediatr. (1987); 146:21-26.
Massaro, et al., "Hunger disease and pulmonary alveoli." Am J Respir Crit Care Med. (2004); 170(7): 723-724.
Massaro, et al., "Lung alveoli: endogenous programmed destruction and regeneration." Am J Physiol Lung Cell Mol Physiol. (2002); 283(2): L305-9.
Masumoto, et al., "Nutritional management in neonatal patients." Parenteral and Enteral Nutrition (2012); 27(5): 1195-1201 (and English translation of pertinent portion(s)).
Mataloun, et al., "Pulmonary responses to nutritional restriction and hyperoxia in premature rabbits." J Pediatr (Rio J). (2006); 82(3): 179-185.
McKiernan and Hull, "The Constituents of Neonatal Milk," Pediatr. Res. 16:60-64 (1982).
Melegh, et al., "Changes of Plasma Free Amino Acids and Renal Clearances of Carnitines in Premature Infants During L-Carnitine-Supplemented Human Milk Feeding", J. Pediatric Gastroenterol. Nutr. 7(3):424-429 (1998).
Mendenhall et al., "Protein-calorie malnutrition associated with alcoholic hepatitis", The American Journal of Medicine, 76(2): 211-222 (1984).
Mendenhall et al., "VA cooperative study on alcoholic hepatitis. II: Prognostic significance of protein-calorie malnutrition", Am J Clin Nutr, 43(2): 213-218 (1986).
Morgan et al., "Nutrition in cryptogenic cirrhosis and chronic aggressive hepatitis", Gut, 17: 113-118 (1976).
Moro et al., "Fortification of Human Milk: Evaluation of a Novel Fortification Scheme and of a New Fortifier," J. Ped. Gastroenterol. Nutr. 20:162-172 (1995).
Moro, G.E., et al., "Growth and Metabolic Responses in Low-Birth-Weight Infants Fed Human Milk Fortified with Human Milk Protein or with a Bovine Milk Protein Preparation," J. Pediatric Gastroenterol. and Nutr. 1991. vol. 13, pp. 150-154.
Morrow, et al., "Human milk oligosaccharides are associated with protection against diarrhea in breast-fed infants." The Journal of Pediatrics (2004); 145(3): 297-303.
Muscaritoli, Maurizio, et al. "Clinical and metabolic effects of different parenteral nutrition regimens in patients undergoing allogeneic bone marrow transplantation." Transplantation (1998); 66.5: 610-616.
OGUNDELE,"Techniques for the storage of human breast milk: implications for anti-microbial functions and safety of stored milk," Eur. J. Pediatr. 159:793-797 (2000).
Oh, et al., "Neonatal Research Network: Association between fluid intake and weight loss during the first ten days of life and risk of bronchopulmonary dysplasia in extremely low birth weight infants." J Pediatr. (2005); 147(6): 786-790.
O'Keefe et al., "Malnutrition and immuno-incompetence in patients with liver disease", Lancet, 316(8195): 615-617 (1980). Originally published as vol. 2, Issue 8195.).

Palombo et al., "Effectiveness of orthotopic liver transplantation on the restoration of cholesterol metabolism in patients with end-stage liver disease", Gastroenterology, 93(6): 1170-1177 (1987).
Panzer et al., "Immune thrombocytopenia in severe hemophilia A treated with high-dose intravenous immunoglobulin," Transfusion 26:69-72 (1986).
Partial Supplementary European Search Report for European Patent Application No. 15876253.4, dated Jul. 24, 2018, 11 pages.
PCT/US2006/036827, International Search Report and Written Opinion, 8 pages, dated Sep. 5, 2007, 8 pages.
PCT/US2007/019234, International Search Report and Written Opinion, 6 pages, dated Jan. 18, 2008, 6 pages.
PCT/US2007/085969, International Search Report and Written Opinion, 8 pages, dated May 8, 2008, 8 pages.
PCT/US2007/086973, International Preliminary Report on Patentability, dated Jun. 10, 2009, 7 pages.
PCT/US2007/086973, International Search Report and Written Opinion, 8 pages, dated May 5, 2008, 8 pages.
PCT/US2009/066430, International Search Report and Written Opinion of the International Searching Authority, 11 pages, dated Jan. 26, 2010, 11 pages.
PCT/US2012/049590, International Search Report, 2 pages, dated Oct. 1, 2012, 2 pages.
PCT/US2012/049590, Written Opinion, 6 pages, dated Oct. 1, 2012, 6 pages.
PCT/US2014/020837, International Preliminary Report on Patentability dated Sep. 15, 2015, 6 pages.
PCT/US2014/020837, International Search Report and Written Opinion dated Jun. 10, 2014, 7 pages.
PCT/US2015/068050, International Preliminary Report on Patentability dated Jul. 4, 2017, 9 pages.
PCT/US2015/068050, International Search Report and Written Opinion dated Mar. 4, 2016, 10 pages.
PCT/US2016/027893, International Preliminary Report on Patentability dated Oct. 17, 2017, 10 pages.
PCT/US2016/027893, International Search Report and Written Opinion dated Jul. 15, 2016, 11 pages.
PCT/US2016/069250, International Preliminary Report on Patentability dated Jul. 3, 2018, 9 pages.
PCT/US2016/069250, International Search Report and Written Opinion dated Mar. 30, 2017, 15 pages.
Pham and Lawley, "Emerging insights on intestinal dysbiosis during bacterial infections." Current Opinion in Microbiology (2014); 17: 67-74. Epub Dec. 29, 2013.
Pietz, J., et al., "Prevention of Necrotizing Enterocolitis in Preterm Infants: A 20-Year Experience." Pediatrics (2007); 119 (1): e164-e170, 9 pages.
Polberger, S.K.T., "Fortified Human Milk for Very Low Birth Weight Infants: Effects on Growth and Metabolism," Dept. Pediatrics, University of Lund, Malmo 1990, pp. 1-148.
Polberger, S.K.T., et al., "Amino Acid Concentrations in Plasma and Urine in Very Low Birth Weight Infants Fed Non-Protein-Enriched or Human Milk Protein-Enriched Human Milk," Department of Pediatrics, University of Lund, Malmö General Hospital, S-21401 Malmö Sweden, pp. 131-148. Pediatrics 1990; 86:909-915.
Polberger, S.K.T., et al., "Assessment of Eleven Different Plasma Proteins as Indicators of Protein Nutritional Status in Very Low Birth Weight Infants," Department of Pediatrics, University of Lund, Malmö General Hospital, S-21401 Malmö Sweden, 1990, pp. 115-129.
Polberger, S.K.T., et al., "Concentrations of Twelve Plasma Proteins at Birth in Very Low Birth Weight and in Term Infants," Department of Pediatrics, University of Lund, Malmö General Hospital, S-21401 Malmö Sweden, pp. 101-114. Acta Paediatr Scand. 1990; 79(8-9): 729-736.
Polberger, S.K.T., et al., "Growth of Very Low Birth Weight Infants on Varying Amounts of Human Milk Protein," Department of Pediatrics, University of Lund, Malmö General Hospital, S-21401 Malmö Sweden, pp. 69-87. Pediatr Res 1989; 25: 414-419.
Polberger, S.K.T., et al., "Urinary and Serum Urea as Indicators of Protein Metabolism in Very Low Birth Weight Infants Fed Varying Human Milk Protein Intakes," Department of Pediatrics, University

(56) References Cited

OTHER PUBLICATIONS of Lund, Malmö General Hospital, S-21401 Malmö Sweden, pp. 89-99. Acta Paediatr Scand. 1990; 79(8-9): 737-42.
Prentice, A., "Constituents of Human Milk," Food and Nutrition Bulletin, the United Nations University Press, 17(4), Dec. 1996.
Ronnholm, K., et al., "Supplementation with Human Milk Protein Improves Growth of Small Premature Infants Fed Human Milk," Pediatrics. 1986. vol. 77, No. 5, pp. 649-653.
Ronnholm, K.A.R., et al., "Human Milk Protein and Medium-Chain Triglyceride Oil Supplementation of Human Milk: Plasma Amino Acids in Very Low-Birth-Weight-Infants," Pediatrics, American Academy of Pediatrics, 74(5)792-799, Jan. 1, 1984.
Rüdiger, et al., "Preterm infants with high polyunsaturated fatty acid and plasmalogen content in tracheal aspirates develop bronchopulmonary dysplasia less often." Crit Care Med. (2000); 28(5): 1572-1577.
Russell, et al., "Cost of hospitalization for preterm and low birth weight infants in the United States." Pediatrics (2007); 120(1): e1-9.
Saiki et al., "Genetic analysis of amplified DNA with immobilized sequence-specific oligonucleotide probes," Proc. Natl. Acad. Sci. USA 86:6230-6234 (1989).
Salle, et al., "Effects of Calcium and Phosphorus Supplementation on Calcium Retention and Fat Absorption in Preterm Infants Fed Pooled Human Milk", (1986) J. Pediatric Gastroenterol. Nutr. 5(4):638-642.
Schanler et al., "Feeding strategies for premature infants: beneficial outcomes of feeding fortified human milk versus preterm formula," Pediatr. 103(6 Pt 1):1150-1157 (1999).
Schanler, "Mother's Own Milk, Donor Human Milk, and Preterm Formulas in the Feeding of Extremely Premature Infants." Journal of Pediatric Gastroenterology and Nutrition (2007); 45 (Suppl 3): S175-S177.
Schanler, et al., "Outcomes of human milk-fed premature infants." Semin Perinatal (2011); 35(1): p. 29-33.
Schanler, R., et al., "Enhanced Fecal Excretion of Selected Immune Factors in Very Low Birth Weight Infants Fed Fortified Human Milk," Pediatric Research. 1986. vol. 20, No. 8, pp. 711-715.
Schanler, R., et al., "Fortified Mothers' Milk for Very Low Birth Weight Infants: Results in Macromineral Balance Studies," J. Pediatrics. 1985. vol. 107, No. 5, pp. 767-774.
Schanler, R., et al., "Fortified Mothers' Milk for Very Low Birth Weight Infants; Results of Growth and Nutrient Balance Studies," J. Pediatrics. 1985. vol. 107, No. 3, pp. 437-444.
Schanler, R., et al., "Mineral Balance Studies in Very Low Birth Weight Infants Fed Human Milk," J. Pediatrics. 1988. vol. 113, vol. 1, Part 2, pp. 230-238.
Sears, Martha, et al., "The Breastfeeding Book", Jiangsu Literature and Art Publishing House, pp. 242-245, Jan. 2011, with English translation, 6 pages.
Srinivasan, L., et al., "Increased Osmolality of Breast Milk with Therapeutic Additives," Arch Dis Child Fetal Neonatal Ed. 2004. 89:F514-517.
Sullivan, et al., "An exclusively human milk-based diet is associated with a lower rate of necrotizing enterocolitis than a diet of human milk and bovine milk-based product." J Pediatr. (2010); 156(4):562-567.e1.
Supplementary European Search Report dated Apr. 20, 2011 in co-pending European application No. EP 07811645.6, 7 pages.
Supplementary European Search Report dated Apr. 27, 2011 in co-pending European application No. EP 07864921.7, 8 pages.
Supplementary European Search Report dated Mar. 24, 2009 in co-pending European application No. EP 06815100.0, 6 pages.
Supplementary European Search Report dated Oct. 15, 2010, in co-pending related European application No. EP 07865463.9, 6 pages.
Supplementary European Search Report dated Oct. 29, 2012 in co-pending European application No. EP 09831061.8, 5 pages.

Terpstra, et al., "Antimicrobial and Antiviral Effect of High-Temperature Short-Time (HTST) Pasteurization Applied to Human Milk," Breastfeeding Med. 2007. vol. 2, pp. 27-33.
The Dairy Council, "The Nutritional Composition of Dairy Products," pp. 1-49, 2002.
Theile, et al., "Nutritional strategies and growth in extremely low birth weight infants with bronchopulmonary dysplasia over the past 10 years." J Perinatol. (2012); 32(2): 117-122.
Tully, "Is Pasteurized Mother's Own or Donor Milk an Answer to the HIV Crisis," J. Hum. Lact. 15(4):345-346 (1999).
U.S. National Library Of Medicine: "Archive History for NCT02025478 Human Breastmilk in Children Receiving a Bone Marrow Transplant", Mar. 25, 2015 (Mar. 25, 2015), XP055518058, Retrieved from the Internet: URL:https://clinicaltrials.gov/ct2/history/NCT02025478?V 2=View#StudyPageTop [retrieved on Oct. 23, 2018], 6 pages.
Vieira, et al., "Analysis of the influence of pasteurization, freezing/thawing, and offer processes on human milk's macronutrient concentrations." Early Hum Dev. (2011); 87(8): 577-580.
Virus Safety Services, Sanquin Research, Final Report FR4500, "Process Validation Breast Milk Step 1 for Inactivation of BVDV/HAV/HIV/PSR," May 27, 2002, pp. 1-33.
Voyer, M., et al. "Human Milk Lacto-Engineering," Acta Paediatr Scan. 1984. vol. 73, pp. 302-306.
Wemhöner, et al., "Nutrition of preterm infants in relation to bronchopulmonary dysplasia." BMC Pulm Med. (2011); 11: 7.
Wight, N.E., et al., Best Medicine: Human Milk in the NICU (2008); pp. xi-xiv, pp. 1-7, pp. 9-32, pp. 43-96, 91 pages.
Williams et al., "Human Milk Banking," J. Trap. Pediatr. 31:185-190 (1985).
Wojcik, et al., "Macronutrient analysis of a nationwide sample of donor breast milk." J Am Diet Assoc. (2009); 109(1): 137-140.
Yunghans, Regina, "8 Alternative Uses for Breastmilk-alternative-uses-for-breastm", Jul. 8, 2011 (Jul. 8, 2011), XP055325257, Retrieved from the Internet: URL:http://www.thekitchn.com/8-alternative-uses-for-breastm-150830 [retrieved on Dec. 1, 2016] * the whole document *.
Zimmerman, Edith, "But What Does Breastmilk Cheese Taste Like?" Jan. 18, 2011 (Jan. 18, 2011), pp. 1-3, XP055324917, Retrieved from the Internet: URL:https://thehairpin.com/but-what-does-breastmilk-cheese-taste-like-3df200ea554b#.qkxr5lv8e [retrieved on Nov. 30, 2016] * the whole document*.
[Author Unknown], Fifth Revised and Enlarged Edition, Standard Tables of Food Composition in Japan, Oct. 10, 2009, Second edition, Third printing, pp. 188-193 (with portions in English language), 7 pages.
Extended European Search Report for European Patent Application No. 20216091.7 dated Mar. 29, 2021, 11 pages.
Ireton-Jones, Carol S., "Intake: Energy". In: Krause's and Mahan's Food & The Nutrition Care Process, (eds.) Janice L. Raymond and Kelly Morrow, 15th Edition (2021); Chapter 2, pp. 17-27, 14 pages.
Kuschel, et al., "Fat supplementation of human milk for promoting growth in preterm infants." Cochrane Database of Systematic Reviews (Apr. 24, 2000); 3 pages, DOI: 10.1002/14651858. CD000341, www.cochranelibrary.com/cdsr/doi/10.1002/14651858. CD000341/full.
Polberger, S.K.T., et al., "Growth of Very Low Birth Weight Infants on Varying Amounts of Human Milk Protein," Pediatric Research (1989); 25(4): 414-419.
Prolact CR® label, Human Milk Caloric Fortifier (Human, Pasteurized), 10 mL, Prolacta Bioscience, Inc., California, USA (2018), 2 pages.
Merck Manual of Diagnosis & Therapy, 18th Edition, Japanese Version, Nikkei Business Publications, Inc., Apr. 25, 2007, 1st Printing, 3rd Impression, pp. 2441-2442, and English translation of pertinent portions, 6 pages.

\* cited by examiner

*poor weight gain is defined as <20g/day

Feeding Intolerance Algorithm for Neonates with Congenital Heart Disease

FIGURE 5

DBM Transition Protocol

| Feeding Schedule Q 3hr Feedings: | Last Day of all Human milk | Transition Day 1 EBM/Formula & DBM (or formula can be mixed as 25% of total feed) | Transition Day 2 EBM/Formula & DBM (or formula can be mixed as 50% of total feed) | Transition Day 3 EBM/Formula & DBM (or formula can be mixed as 75% of total feed) | Transition Day 4 100% Transition to human milk fortified to 24kcal/oz w/ formula or 24kcal/oz Fortified Formula |
|---|---|---|---|---|---|
| 1 | Human milk+ PBCLN-002 | 24kcal/oz Hum Milk or Formula | 24kcal/oz Hum Milk or Formula | 24kcal/oz Hum Milk or Formula | 24kcal/oz Hum Milk or Formula |
| 2 | Human milk+ PBCLN-002 | Human milk+ PBCLN-002 | Human milk+ PBCLN-002 | 24kcal/oz Hum Milk or Formula | 24kcal/oz Hum Milk or Formula |
| 3 | Human milk+ PBCLN-002 | Human milk+ PBCLN-002 | 24kcal/oz Hum Milk or Formula | 24kcal/oz Hum Milk or Formula | 24kcal/oz Hum Milk or Formula |
| 4 | Human milk+ PBCLN-002 | Human milk+ PBCLN-002 | Human milk+ PBCLN-002 | Human milk+ PBCLN-002 | 24kcal/oz Hum Milk or Formula |
| 5 | Human milk+ PBCLN-002 | 24kcal/oz Hum Milk or Formula | 24kcal/oz Hum Milk or Formula | 24kcal/oz Hum Milk or Formula | 24kcal/oz Hum Milk or Formula |
| 6 | Human milk+ PBCLN | Human milk+ PBCLN-002 | Human milk+ PBCLN-002 | 24kcal/oz Hum Milk or Formula | 24kcal/oz Hum Milk or Formula |
| 7 | Human milk+ PBCLN-002 | Human milk+ PBCLN-002 | 24kcal/oz Hum Milk or Formula | 24kcal/oz Hum Milk or Formula | 24kcal/oz Hum Milk or Formula |
| 8 | Human milk+ PBCLN-002 | Human milk+ PBCLN-002 | Human milk+ PBCLN-002 | Human milk+ PBCLN-002 | 24kcal/oz Hum Milk or Formula |

- If EBM is available transition to EBM fortified to 24kcal/oz with term formula. If standard of care is to discharge on donor human milk at that facility then it can be used
- If no EBM is available transition to TERM formula fortified to 24kcal/oz
- TERM Formula to be used can be chosen per facility by Dietitian or Cardiac team, Minimum concentration of 20 cal/oz during intervention period
- Direct breast feeding may be incorporated into feeding regimen per facility

HUMAN MILK PRODUCTS USEFUL IN PRE- AND POST-OPERATIVE CARE

CROSS REFERENCE TO RELATED APPLICATIONS

This application is a U.S. national phase application of International Application No. PCT/US2016/069250, filed Dec. 29, 2016, which claims priority to, and the benefit of U.S. Provisional Application No. 62/273,243 filed Dec. 30, 2015, the contents of which are incorporated herein by reference in their entireties.

FIELD OF THE INVENTION

The present disclosure relates to human milk compositions and methods of making and using the same. In particular, the disclosure features methods of using human milk compositions to feed subjects before and/or after surgery or medical operations and that are useful in promoting recovery and decreasing the length of time the subjects must spend in the hospital. Thus, also provided herein are methods of promoting recovery of a subject, particularly an infant, following surgery by feeding those subjects one or more of the compositions described herein.

BACKGROUND OF THE INVENTION

Human milk is the ideal source of nutrition for premature infants, providing benefits in host defense, gastrointestinal maturation, infection rate, neurodevelopmental outcomes, and long-term cardiovascular and metabolic disease (Schanler, R. J., Outcomes of human milk-fed premature infants. Semin Perinatol, 2011. 35(1): p. 29-33). An exclusive human milk (HM)-based diet significantly decreases the rates of necrotizing enterocolitis (NEC), sepsis, days of parenteral nutrition, and death (Sullivan, S., et al., *An exclusively human milk-based diet is associated with a lower rate of necrotizing enterocolitis than a diet of human milk and bovine milk-based products.* J Pediatr, 2010. 156(4): p. 562-567.e1; Cristofalo, E. A., et al., *Randomized trial of exclusive human milk versus preterm formula diets in extremely premature infants.* The Journal of Pediatrics, 2013(163): p. 1592-1595; Abrams, S. A., et al., *Greater Mortality and Morbidity in Extremely Preterm Infants Fed a Diet Containing Cow Milk Protein Products.* Breastfeeding Medicine, 2014. 9(6): p. 281-285).

Medical nutrition therapy is an important consideration for patient populations at risk of malnutrition. This is of particular importance for infants undergoing surgery as these infants are at an increased risk for growth failure, developmental delays, necrotizing enterocolitis, poor wound healing and late onset sepsis, with the risk increasing with earlier gestational age and lower birth weight as well as those infants who require surgery soon after birth. Human milk is generally the food of choice for all infants, regardless of gestational age at birth because of its nutritional composition and immunological benefits.

Breast milk may also be the optimal nutrition for pre- and post-surgical infants because of its ease of digestibility, nutritional composition, immunologic components and anti-infective benefits. (See, AAP COMMITTEE ON NUTRITION, AAP SECTION ON BREASTFEEDING, AAP COMMITTEE ON FETUS AND NEWBORN. *"Donor Human Milk for the High-Risk Infant: Preparation, Safety, and Usage Options in the United States."* Pediatrics. 2017; 139(1):e20163440) Furthermore, infants undergoing surgery often fail to tolerate feeding regimens due to intolerance of artificial infant formulas resulting in complete or partial supplementation with total parenteral nutrition (TPN) for extended periods of time increasing the risk of metabolic derangements and TPN-associated complications.

Infants in need of surgery soon after birth include infants with congenital birth defects affecting the major organs such as the heart, such as hypoplastic left heart syndrome and the intestine, such as gastroschisis and omphalocele as well as infants that develop conditions requiring surgery after birth, including infants that develop necrotizing enterocolitis (NEC).

Even when infants are able to tolerate breast milk feeding in and around the time of surgery, unfortified human milk does not meet the nutritional needs of many of these infants necessitating supplementation, for example with TPN. The use of TPN and incomplete enteral breast milk feeding may result in intestinal brush border dysfunction, dysbiosis (heavy growth of harmful bacteria in the intestine), metabolic disorders as well as TPN-related liver disease hindering post-op recovery and impacting long term development. This is a particular concern when the infant's condition necessitates fluid restriction, as is often the case with infants with congenital heart disease. Recent data has shown that the energy content of human milk often falls below generally accepted value of 20 kcal/oz (Wojcik, K. Y., et al., *Macronutrient analysis of a nationwide sample of donor breast milk.* Journal of the American Dietetic Association, 2009. 109(1): p. 137-140; Vieira, A. A., et al., *Analysis of the influence of pasteurization, freezing/thawing, and offer processes on human milk's macronutrient concentrations.* Early Human Development, 2011. 87(8): p. 577-580). As a result, the expected energy and nutrient content may not be achievable in pen-operative infants, particularly those with congenital heart disease where total fluid intake is restricted. Due to the increased energy and macronutrient requirements of this population when compared to the normal infants, the ability to provide the extra calories is an important step toward therapeutic intervention in the nutritional management of pre and post-surgical infants.

Thus, a nutritional solution is needed to prepare and assist infants in recovery from surgery, particularly those who must maintain a fluid restricted diet.

SUMMARY OF THE INVENTION

The current invention provides a high energy/high fat human milk composition that can be administered orally or enterally to increase the caloric content of human donor milk or mother's own milk while not substantially increasing the overall volume or osmotic load necessary to meet the nutritional requirements of these infants. The opportunity for an exclusive human milk diet in infants requiring surgery thereby improves short and long term clinical outcomes including improved growth velocity and wound healing resulting in a decreased length of hospital stay (LOS) and improved neurodevelopment.

This disclosure features human milk compositions and methods of making and using such compositions. In some embodiments the human milk composition is a human milk fortifier. In some embodiments, the human milk composition comprises milk and human milk fortifier. In some embodiments, the milk is human mother's milk. In other embodiments, the milk is pooled human milk. In some embodiments, the milk is a ready-to-feed product. In other embodiments, the milk is non-human. In some embodiments, the human milk composition comprises infant formula.

The present invention provides human milk compositions comprising from about 19 mg/mL to about 26 mg/mL protein, from about 49 mg/mL to about 64 mg/mL fat, and from about 81 mg/mL to about 97 mg/mL carbohydrates. In another embodiment, the human milk composition comprises about 24 to about 26 mg/mL protein, from about 60 mg/mL to about 64 mg/mL fat, and from about 83 mg/mL to about 97 mg/mL carbohydrates. In another embodiment, the human milk composition comprises about 19 to about 20 mg/mL protein, from about 49 mg/mL to about 51 mg/mL fat, and from about 81 mg/mL to about 89 mg/mL carbohydrates. In another embodiment, the human milk composition comprises about 21 to about 23 mg/mL protein, from about 54 to about 57 mg/mL fat, and about 82 to about 89 mg/mL carbohydrates.

In one embodiment, the method provides administering to a subject a human milk composition comprising from about 19 mg/mL to about 26 mg/mL protein, from about 49 mg/mL to about 64 mg/mL fat, and from about 81 mg/mL to about 97 mg/mL carbohydrates. In another embodiment, the method provides administering to a subject a human milk composition comprising about 24 to about 26 mg/mL protein, from about 60 mg/mL to about 64 mg/mL fat, and from about 83 mg/mL to about 97 mg/mL carbohydrates. In another embodiment, the method provides administering to a subject a human milk composition comprising about 19 to about 20 mg/mL protein, from about 49 mg/mL to about 51 mg/mL fat, and from about 81 mg/mL to about 89 mg/mL carbohydrates. In another embodiment, the method provides administering to a subject a human milk composition comprises about 21 to about 23 mg/mL protein, from about 54 to about 57 mg/mL fat, and about 82 to about 89 mg/mL carbohydrates.

In one embodiment, the human milk composition provides from about 67 to about 139 kcal/kg/day. In another embodiment, the human milk composition provides from about 80 to about 130 mL/kg/day. In another embodiment, the human milk composition provides from about 90 to about 100 mL/kg/day.

In one embodiment, the human milk composition further comprises one or more constituents selected from the group consisting of: calcium, chloride, copper, iron, magnesium, manganese, phosphorus, potassium, selenium, sodium, and zinc. In another embodiment, the human milk composition further comprises human milk oligosaccharides.

In one embodiment, the human milk composition is administered to the subject orally. In another embodiment, the human milk composition is administered to the subject enterally.

In one embodiment, said subject is a human child, or infant. In a particular embodiment, the child is from about 18 years old to about 2 years old. In other embodiments, said subject is a child about two years old or younger. In another embodiment, said subject is less than or equal to 7 days old. In still other embodiments, said subject is a premature infant. In some embodiments, said subject is a human adult. In one embodiment, the human adult is 18 years old or older.

In one aspect, the method comprises providing nutrition to a subject who is undergoing or has undergone surgery. In a further aspect, the method comprises administering to a subject a human milk composition comprising a fortifier composition. In one embodiment, the human milk composition provides about 70% of the total nutrition and the fortifier composition provides about 30% of the total nutrition. In another embodiment, the human milk composition provides about 60% of the total nutrition and the fortifier composition provides about 40% of the total nutrition. In another embodiment, the human milk composition provides about 50% of the total nutrition and the fortifier composition provides about 50% of the total nutrition.

Human milk is defined as expressed breast milk or donor milk and its derivatives, human milk-based fortifier and human milk caloric fortifier. Standard human milk formulation include Prolact-RTF™, PROLACTPLUS™ PROLACT+4®, PROLACT+6®, PROLACT+8®, and/or PROLACT+10®, which are produced from human milk and contain various concentrations of nutritional components.

The disclosure features standardized human milk formulations or fortifiers, which are produced from human milk. Methods of making and using such compositions are also described herein. In some embodiments, standardized human milk formulations are supplemented with vitamins and/or minerals. In some embodiments, the standardized milk formulations are fed orally to subjects who are undergoing or have undergone surgery. The methods of generating these compositions are designed to optimize the amount of nutrients and calories in the compositions.

In some embodiments, the human milk compositions further comprise one or more constituents selected from the group consisting of: calcium, chloride, copper, iron, magnesium, manganese, phosphorus, potassium, selenium, sodium, and zinc.

In one aspect, the disclosure features a human milk fortifier composition comprising: a human protein constituent from about 35 mg/mL to about 45 mg/mL and a human fat constituent from about 80 mg/mL to about 100 mg/mL. In one aspect, the disclosure features a human milk fortifier composition comprising: a human protein constituent from about 35 mg/mL to about 42 mg/mL and a human fat constituent from about 84 mg/mL to about 95 mg/mL. In another aspect, the disclosure features a human milk fortifier composition comprising: a human protein constituent of about 37 to about 42 mg/mL and a human fat constituent of about 86 to about 94 mg/mL. In another aspect, the disclosure features a human milk fortifier composition comprising: a human protein constituent of about 39.2 mg/mL and a human fat constituent of about 94.5 mg/mL. The carbohydrate constituent can include additional lactose. In some embodiments, the composition further comprises one or more constituents selected from the group consisting of: calcium, chloride, copper, iron, magnesium, manganese, phosphorus, potassium, selenium, sodium, and zinc.

In one aspect, a method for obtaining a human milk composition is provided. In some embodiments, the method includes: (a) genetically screening human milk for one or more viruses; (b) optionally filtering the milk; (c) optionally heat-treating the milk, e.g., at about 63° C. or greater for about 30 minutes; (d) separating the milk into cream and skim; (e) adding a portion of the cream to the skim; and (f) pasteurizing or otherwise sterilizing the composition.

In some embodiments, the genetic screening in step (a) is polymerase chain reaction and/or includes screening for one or more viruses, e.g., human immunodeficiency virus Type 1 (HIV-1), hepatitis B virus (HBV), and/or hepatitis C virus (HCV).

In some embodiments, the milk is optionally filtered through an about 200-micron screen in step (b).

In some embodiments, the method further includes running cream, e.g., about 30-70% fat in the cream, through a separator following step (d). In one embodiment, the method further includes filtering the skim through filters after step (d), e.g., to filter the water out of the skim. In some embodiments, after filtering the skim after step (d), the filters used in the filtering is washed to obtain a post wash solution. In further embodiments, the post wash solution is added to the skim.

In some embodiments, the method further includes carrying out mineral analysis of the portion of the composition obtained after step (e). In one embodiment, the method also includes adding to the composition obtained after step (e) one or more minerals selected from the group consisting of: calcium, chloride, copper, iron, magnesium, manganese, phosphorus, potassium, selenium, sodium, and zinc. Adding of the one or more minerals includes heating the composition, in some embodiments.

In a particular embodiment, the method also includes cooling the composition after step (f), carrying out biological testing of a portion of the composition after step (f), and/or carrying out nutritional testing of a portion of the composition after step (f).

In some embodiments, the human milk of step (a) is pooled human milk. Thus, in some embodiments, the methods provided herein are carried out with large volumes of the starting material, e.g., human milk, e.g., pooled human milk. In some embodiments, the volumes can be in the range of about 75 liters/lot to about 10,000 liters/lot of starting material (e.g. about 2,500 liters/lot or about 2,700 liters/lot or about 3,000 liters/lot or about 5,000 liters/lot or about 7,000 liters/lot, about 7,500 liters/lot or about 10,000 liters/lot).

In another aspect, the disclosure features a method for obtaining a human milk composition. The method includes: (a) genetically screening human milk for one or more viruses; (b) filtering the milk; (c) adding cream; and (d) pasteurizing.

In one embodiment, the genetic screening in step (a) is a polymerase chain reaction. In some embodiments, the genetic screening includes screening for one or more viruses, e.g., HIV-1, HBV, and/or HCV.

In one embodiment, the milk is optionally filtered through an about 200 micron screen in step (b). In some embodiments, the method further includes ultra-filtering the whole milk after step (b) through filters. In some embodiments, the filters used during ultra-filtering are post washed. In some embodiments, the filters used during ultra-filtration are post washed with permeate. In some embodiments, the filters used during ultra-filtration are post washed with water.

In some embodiments, the composition is cooled after step (d). In some embodiments, biological and/or nutritional testing of the composition is carried out after step (d).

In some embodiments, the human milk of step (a) is pooled human milk. Thus, in some embodiments, the methods featured herein are carried out with large volumes of the starting material, e.g., human milk, e.g., pooled human milk. In some embodiments, the volumes are in the range of about 75-10,000 liters/lot of starting material. In a particular embodiment, the volume is about 2,000 liters/lot. In another embodiment, the volume is about 2,500 liters/lot. In another embodiment, the volume is about 2,700 liters/lot. In another embodiment, the volume is about 3,000 liters/lot. In another embodiment, the volume is about 4,000 liters/lot. In still another embodiment, the volume is about 5,000 liters/lot. In still another embodiment, the volume is about 7,000 liters/lot. In still another embodiment, the volume is about 7,500 liters/lot. In still another embodiment, the volume is about 10,000 liters/lot.

In some embodiments, the method includes adding to the composition obtained after step (c) one or more minerals selected from the group consisting of: calcium, chloride, copper, iron, magnesium, manganese, phosphorus, potassium, selenium, sodium, and zinc.

In one aspect, a method is provided for improving one or more clinical outcomes subjects recovering from surgery. In some embodiments, the one or more improved clinical outcomes comprise short and/or long term benefits. In certain embodiments, the one or more improved clinical outcomes are selected from improved neurodevelopmental outcomes, improved growth velocity including rate of weight gain, incremental linear growth, incremental rate of head circumference growth, reduced length of stay in the hospital and a reduction of the days of parenteral nutrition. In some embodiments, the one or more improved clinical outcomes is selected from reduced incidence and/or severity of feeding intolerance, reduced incidence and/or severity of sepsis, reduced incidence and/or severity of necrotizing enterocolitis (NEC), rediced incidence and/or severity of wound infections, and/or wound dehiscence. Thus, in one aspect, methods for improving the clinical outcome of subjects, particularly infants, recovering from surgery is provided.

BRIEF DESCRIPTION OF THE DRAWINGS

FIG. 5 is a chart of the weaning schedule.

DETAILED DESCRIPTION OF THE INVENTION

Figure 1:
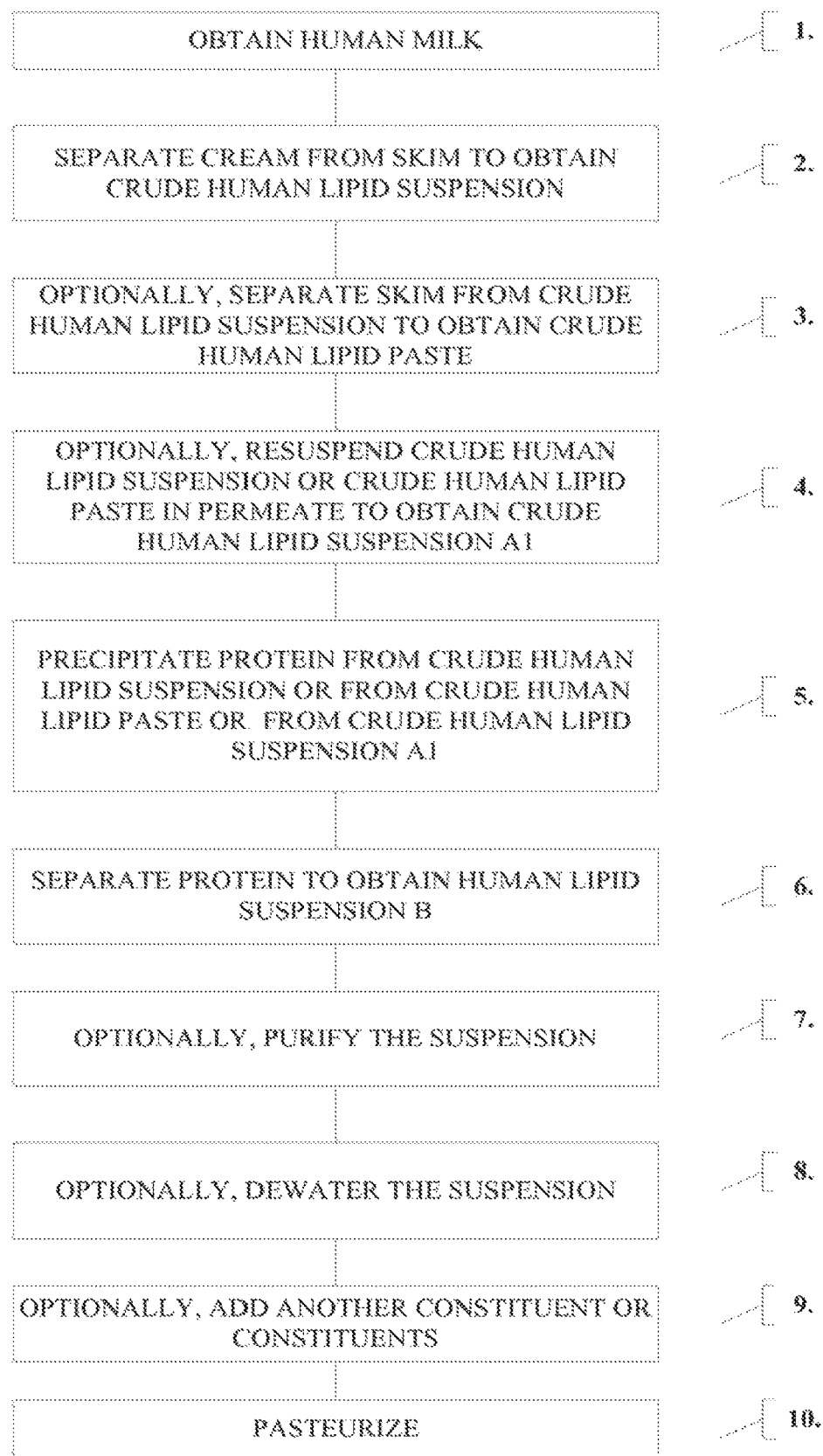
FIG. 1 is a flow chart showing the method of fortifier production.

This disclosure features human milk compositions, e.g., a human milk fortifier, human milk fortifier mixed with mother's own milk and standardized ready to feed human milk compositions, as well as methods of making and using such compositions.

This disclosure also features standardized human milk formulations, which are produced from human milk. Methods of making and using such compositions are also described. These standardized human milk formulations can be used to feed subjects who are undergoing or have undergone surgery, with or without mixing them with other fortifiers or milk, for instance mother's own milk. Human milk formulations can contain various caloric contents, for example, the human milk compositions described herein can provide from about 67 to about 139 kcal/kg/day, for example from about 90 to about 100 kcal/kg/day.

The compositions of the present disclosure are generated from human donor milk, e.g., pooled milk, which undergoes rigorous genetic screening, processing (e.g., to concentrate nutrients in the fortifier compositions, and/or to reduce bioburden), and pasteurization. The milk can be supplemented with various minerals and/or vitamins. Thus, the disclosure also features methods of obtaining and processing milk from human donors.

The methods of the present disclosure can be used to process large volumes of donor milk, e.g., about 75-7,500 liters/lot of starting material. In a particular embodiment, the volume is about 2,000 liters/lot. In another embodiment, the volume is about 2,500 liters/lot. In another embodiment, the volume is about 2,700 liters/lot. In another embodiment, the volume is about 3,000 liters/lot. In another embodiment, the volume is about 4,000 liters/lot. In still another embodiment, the volume is about 5,000 liters/lot. In still another embodiment, the volume is about 7,000 liters/lot. In still another embodiment, the volume is about 7,500 liters/lot. In still another embodiment, the volume is about 10,000 liters/lot.

As used herein, the term "adulterant" refers to any non-human milk found in human milk. The addition of adulterants to human milk is referred to as "adulteration". Examples of adulterants include milk from non-human species (e.g., cow milk, goat milk, etc.), milk-like products from plants (e.g., soy milk) and infant formula.

As used herein, the term "contaminant" refers to the inclusion of unwanted substances in human milk. While an adulterant is a "contaminant" generally the use of the term "contaminant" as used herein generally refers to other substances such as drugs, environmental pollutants and/or bacteria and viruses. The inclusion of contaminants to human milk is referred to as "contamination." The inclusion of contaminants may be due to any reason including but not limited to accident, negligence or intent.

As used herein, the terms "surgery" and "surgical procedure" and "surgical operation" and "operation" or "operative care" or "operative procedure" are used interchangeably herein and refer to a medical procedure that uses operative manual and instrumental techniques including any invasive (involving cutting) or non-invasive (i.e. where the internal organs are accessed via a bodily orifice) procedure done on the human body to investigate and/or treat a pathological condition such as disease or injury, to help improve bodily function or appearance or to repair unwanted ruptured areas.

As used herein, the terms "donor" and "individual" are used interchangeably and refer to a woman who supplies or provides a volume of her milk, regardless of whether or not she is compensated, e.g., monetarily, for the milk.

As used herein, the term "full-term" or "term infant" refers to infant born in a range of 37 to 42 weeks gestation.

As used herein, the terms "preterm," "preterm infant," "premature," or "premature infant" are used interchangeably and refer to infants born before 37 weeks.

As used herein, the term "enteral feeding" refers to the delivery of a nutritionally complete feed, containing protein, carbohydrate, fat, water, minerals and vitamins, directly into the stomach, duodenum or jejunum. Typically, in infants too premature to feed via a bottle or otherwise in infants unable to effectively feed from a bottle (either mechanical or functional) short-term delivery of enteral feeds is accomplished via placement of a nasogastric (NG) or nasojejunal (NJ) tube. If oral feedings are delayed for extended periods, more permanent feeding tubes may be placed directly in the stomach as a gastrostomy tube or in the small intestine as a jejunostomy tube.

As used herein, the terms "human milk", "breast milk", "donor milk", and "mammary fluid" are used interchangeably and refer to milk from a human.

As used herein the term "child" or "children" refer to one (or more) human subjects who are under the age of 18.

As used herein the term "infant" refers to a child who is less than 1 year old.

As used herein the term "adult" refers to a human who is 18 years old or older.

As used herein, the term "parenteral nutrition" or refers to feeding a subject intravenously, bypassing the usual process of eating and digestion. Compositions for parenteral nutrition contain nutrients such as glucose, amino acids, vitamins and dietary minerals. Fats are administered separately as a lipid emulsion by central or peripheral vein. Total parenteral nutrition (TPN) may refer to a situation where a patient receives the majority of nutrition via the parenteral route. However, the term TPN is often used in the art as well as herein, synonymously with the nutritional solution used for parenteral nutrition, regardless of the proportion of nutrition derived from this route. Parenteral nutrition may be administered through peripheral vein access in a limb or with a line placed in a large central vein.

As used herein, the term "whole milk" refers to human milk from which no fat has been removed.

As used herein, the term "bioburden" refers to microbiological contaminants and pathogens (generally living) that can be present in milk, e.g., viruses, bacteria, mold, fungus and the like.

As used herein, the term "congenital heart defect", or CHD, refers to a problem with the structure of the heart. Present at birth, congenital heart defects are the most common type of birth defect. The defects can involve the walls of the heart, the valves of the heart, and the arteries and veins near the heart. The heart defects can disrupt the normal flow of blood through the heart and its partitioning to the heart, body and brain. The blood flow can slow down, go in the wrong direction or to the wrong place, or be blocked completely.

The terms "single ventricle physiology" or "single defect anomaly" or "single ventricle defect" refer to a variety of cardiac defects where only one of the heart's two ventricles are present or functions properly. As a result of having only one functioning ventricle, infants with a single ventricle defect have a "Y" shaped circulation where the blood flows from the heart to both the lungs and the body. Further, the working ventricle may be either the left or the right ventricle. Thus, in certain circumstances, it can be difficult to tell which pumping chamber is working properly, making single ventricle physiology among the most complex defects of the heart.

The term "necrotizing enterocolitis" or "NEC" refers to a common and serious intestinal disease in preterm infants. It also occurs at increased frequency in some term infants requiring surgery, for example for serious cardiac malformations. NEC occurs when tissue in the small or large intestine is injured or begins to die off, possibly due to causes such as too little oxygen or blood flow to the intestine at birth, an underdeveloped intestine, injury to the intestinal lining, heavy growth of harmful bacteria in the intestine (dysbiosis) and formula feeding. The inability of the intestine to hold waste once injured could lead to escape of bacteria and other waste products into the infant's bloodstream or abdominal cavity and possible subsequent infection.

The term "sepsis" refers to a potentially life-threatening complication of an infection. Sepsis happens when chemicals released into the bloodstream to fight the infection trigger inflammatory responses throughout the body. This inflammation can trigger a cascade of changes that can damage multiple organ systems, causing them to fail.

By "mixed human milk composition" or "mixed composition" or "mixed formulation" or any human milk product indicated as "mixed" is meant a composition wherein a fortifier has been mixed with a separate milk formulation for use in feeding to an infant. In some embodiments, the fortifiers described herein may be mixed with the infant's mother's own milk, donor milk, a standardized ready to feed human milk formulation or other human or non-human milk or infant formula. A "mixed composition" therefore is a ready to feed composition.

As used herein the term "ready to feed" when used to describe human milk formulations/compositions refers to milk that is ready to be fed to an infant, that is in a form that is suitable for feeding to an infant without further dilution concentrating or mixing (i.e. not a fortifier). In some embodiments, the ready to feed composition is made by mixing a fortifier with pasteurized donor breast milk, mother's own milk, or other standardized pasteurized breast milk formulation. In some embodiments, the ready to feed composition is formulated directly from pooled human milk donations and is provided to the infant in a form that is ready to feed without additional mixing. Such ready-to-feed formulations derive directly from pooled human milk donations and are also referred to as "standardized human milk formulations." The formulations are "standardized" because they contain specific (i.e. standardized) levels of constituents (i.e. fat, protein and carbohydrates). Thus, as used herein "standardized high fat human milk formulations" or "high fat standardized human milk formulations" are ready to feed formulations made directly producing the formulation from pooled human milk donations. While "ready to feed high fat formulations" are made either from mixing a high fat fortifier with ready to feed milk (mother's own milk, donor milk, or other standardized milk formulation) or are made directly from human milk donations.

As used herein "fortifier" means any human milk composition that is added to another milk formulation (human or otherwise) to arrive at a ready to feed formulation.

As used herein the term "pasteurization" refers to any method used to reduce bioburden or otherwise sterilize the human milk for human consumption. Methods of pasteurization include, but in no way are limited to, the use of high temperatures for short periods of time (HTST or "flash" pasteurization), the use of ultra-high temperatures for really short periods of time (UHT). These methods may optionally be combined with homogenization of the milk and/or high pressure treatment of the milk.

Nutritional Requirements of Subjects Preparing for and Recovering from Surgery

Some infants require surgery soon after birth. After completion of surgery, patients are typically transferred directly from the operating room to the neonatal intensive care unit to be closely monitored. When the patient is judged to have recovered from the anesthesia, he/she may also be transferred to a surgical ward or other intensive care unit elsewhere in the hospital. During the post-operative period, the patient's general function and outcome of the procedure are assessed, and the surgical site is checked for bleeding, wound dehiscence or signs of infection. The likelihood of a positive post-operative recovery is linked to nutrition and immune health both prior to the surgery and after. In fact, given the stress on the body and the energy needed to recover, infants that require surgery typically need more calories than an infant without surgery procedures to maintain their basal metabolic levels, to maintain and/or increase growth as well as to heal from the surgery. Milk expressed by mothers of infants delivered after 37 weeks of gestation, however, generally does not meet this increased caloric demand, as its biological function is in the nutrition of a healthy full term infant able to tolerate full volume feeds.

Subjects described herein include human adults, children, and/or infants that have or will undergo surgery. Infants include term and pre-term infants. While the methods and protocols described here are done on 7 day old infants or younger term infant, a person of skill in the art would understand that the compositions and methods would be suitable for older children, adults, and/or preterm infants. One of skill in the art will readily be able to adapt the disclosure herein to meet the nutritional requirements of these older children and adults.

It is critical that the nutritional content of the daily feedings for infants requiring or recovering from surgery meet acceptable levels of key components including total calories and protein contained within a volume they are able to tolerate. In this regard, the nutritional situation for infants requiring or recovering from surgery is similar to that of preterm infants. However, the caloric content of the human milk supplied to infants is very rarely measured but is assumed to be 20 calories/ounce. Traditional human milk fortifiers seek to increase caloric content in part by increasing protein levels. However, while that strategy is appropriate to preterm infants, it may not be appropriate for term infants requiring surgery who are fluid restricted and may not need as much protein for calories as a healthy term infant.

The human milk compositions described herein provide a solution to this problem and may be used to supplement human milk in order to increase the caloric content to the desired level without providing an excess of protein and without increasing the volume to be fed to the infant, and in some instances decreasing the volume fed to the infant. This is particularly useful when all that is needed is increased caloric intake and not increased protein content. Similarly, provided herein are compositions that are standardized high caloric human milk products that contain increased caloric content at similar or decreased volumes compared to donor milk, or mother's own milk, that may be used without fortification. The compositions of the current invention solve this problem by increasing calories without over supplying protein, and therefore, provide a more cost effective solution to the problem while also avoiding possible liver and/or kidney dysfunction associated with excess protein consumption.

The present disclosure features human milk compositions and methods of making and using such compositions for feeding subjects who will undergo or have undergone surgery and who, because of their underlying condition, are fluid restricted. The particular human milk compositions herein provide a unique balance of protein, fat and carbohydrates such that useful calories can be delivered without the need for large volumes of liquid. The human milk compositions can be used to reduce and eliminate the need for TPN.

Human Milk Compositions

The human milk fortifier compositions described herein are produced from whole human milk. The compositions featured herein contain various amounts of nutrients, e.g., protein, carbohydrates, fat, vitamins, and minerals, as well as other milk components. Standardized human milk formulations (including donor milk or mom's own milk) can be supplemented with vitamins and/or minerals if desired and can be fed orally or enterally to subjects who are undergoing or have undergone surgery. The methods of generating these compositions are designed to optimize the amount of nutrients and calories in the compositions.

Human Milk Fortifier

The high energy/high fat human milk fortifier as featured herein can be mixed with human milk or other standardized human milk formulation to produce a fortified human milk formulation suitable for administration to an infant requiring or recovering from surgery. The human milk fortifier as described herein is made according to Table 1:

TABLE 1
Exemplary Human Milk Fortifiers

| Nutrient | Range (mg/mL) |
| --- | --- |
| Fat | 86-94 |
| Protein | 37-42 |
| Carbs | 75-110 |

In some aspect of the current invention, the fortifier described in Table 1 is mixed with human milk (either the infant's mother's own milk, donor milk or a standardized human milk composition, for example, Prolact-RTF™), cow's milk, or infant formula. Preferably, however the fortifier is mixed with fully human milk (e.g. mom's milk, donor milk or Prolact-RTF™). In some embodiments, the human milk fortifier described herein is mixed with human milk at a ratio of 50:50 to yield a mixture that comprises the constituents as listed in Table 2, below. In some embodiments, the human milk fortifier described herein is mixed with human milk at a ratio of 70:30 to yield a mixture that comprises the constituents as listed in Table 3, below. In some embodiments, the human milk fortifier described herein is mixed with human milk at a ratio of 60:40 to yield a mixture that comprises the constituents as listed in Table 4, below. In some embodiments, the human milk fortifier is mixed with cow's milk. In some embodiments, the human milk fortifier described herein is mixed with cow milk at a ratio of 50:50 to yield a mixture that comprises the constituents as listed in Table 2, below. In some embodiments, the human milk fortifier described herein is mixed with cow milk at a ratio of 70:30 to yield a mixture that comprises the constituents as listed in Table 3, below. In some embodiments, the human milk fortifier described herein is mixed with human milk at a ratio of 60:40 to yield a mixture that comprises the constituents as listed in Table 4, below. In some embodiments, the human milk fortifier is mixed with infant formula. In some embodiments, the human milk fortifier described herein is mixed with infant formula at a ratio of 50:50 to yield a mixture that comprises the constituents as listed in Table 2, below. In some embodiments, the human milk fortifier described herein is mixed with infant formula at a ratio of 70:30 to yield a mixture that comprises the constituents as listed in Table 3, below. In some embodiments, the human milk fortifier described herein is mixed with human milk at a ratio of 60:40 to yield a mixture that comprises the constituents as listed in Table 4, below.

Standardized Human Milk Formulations

The standardized human milk formulations featured herein are used to reduce and eliminate the need for TPN for subjects who are undergoing or have undergone surgery. These standardized formulations include various nutritional components for subject growth and development.

Exemplary standardized human milk compositions are found in Tables 2, 3, and 4. These standardized human milk compositions may be made directly from donor milk and supplied in a ready to feed formulation or these compositions may be made by mixing appropriate quantities of the high fat human milk fortifiers described herein with donor milk, mother's own milk, and other ready to feed standardized feeding formulations of human or non-human milk including cow's milk and infant formulas.

TABLE 2
Exemplary Human Milk Composition

| Nutrient | Range (mg/mL) |
| --- | --- |
| Fat | 60-64 |
| Protein | 24-26 |
| Carbs | 83-97 |

TABLE 3
Exemplary Human Milk Composition

| Nutrient | Range (mg/mL) |
| --- | --- |
| Fat | 49-51 |
| Protein | 19-20 |
| Carbs | 81-89 |

TABLE 4
Exemplary Human Milk Composition

| Nutrient | Range (mg/mL) |
| --- | --- |
| Fat | 54-57 |
| Protein | 21-23 |
| Carbs | 82-89 |

Specific Components of the Featured Compositions

One component of the milk compositions featured herein is protein. In the body, protein is needed for growth, synthesis of enzymes and hormones, and replacement of protein lost from the skin, urine and feces. These metabolic processes determine the need for both the total amount of protein in a feeding and the relative amounts of specific amino acids. The adequacy of the amount and type of protein in a feeding for subjects is determined by measuring growth, nitrogen absorption and retention, plasma amino acids, certain blood analytes, and metabolic responses.

Another constituent of the milk compositions described herein is fat. Fat is generally a source of energy for subjects, not only because of its high caloric density but also because of its low osmotic activity in solution.

Vitamins and minerals are important to proper nutrition and development of subjects. A subject requires electrolytes, e.g., sodium, potassium and chloride for growth and for acid-base balance. Sufficient intakes of these electrolytes are also needed for replacement of losses in the urine and stool and from the skin. Calcium, phosphorus and magnesium are needed for proper bone mineralization and growth.

Trace minerals are associated with cell division, immune function and growth. Consequently, sufficient amounts of trace minerals are needed for subject growth and development. Some trace minerals that are important include, e.g., copper, magnesium and iron (which is important, e.g., for the synthesis of hemoglobin, myoglobin and other iron-containing enzymes). Zinc is needed, e.g., for growth, for the activity of numerous enzymes, and for DNA, RNA and protein synthesis. Copper is necessary for, e.g., the activity of several important enzymes. Manganese is needed, e.g., for the development of bone and cartilage and is important in the synthesis of polysaccharides and glycoproteins. Accordingly, the human milk formulations and compositions of the invention can be supplemented with vitamins and minerals as described herein.

Vitamin A is a fat-soluble vitamin essential for, e.g., growth, cell differentiation, vision and proper functioning of the immune system. Vitamin D is important, e.g., for absorption of calcium and to a lesser extent, phosphorus, and for the development of bone. Vitamin E (tocopherol) prevents peroxidation of polyunsaturated fatty acids in the cell, thus preventing tissue damage. Folic acid plays a role in, e.g., amino acid and nucleotide metabolism.

As described above, the variability of human milk vitamin and mineral concentrations often require some fortification to insure that a child is receiving adequate amounts of vitamins and minerals. Examples of vitamins and minerals that can be added to the human milk compositions featured herein include: vitamin A, vitamin B1, vitamin B2, vitamin B6, vitamin B12, vitamin C, vitamin D, vitamin E, vitamin K, biotin, folic acid, pantothenic acid, niacin, m-inositol, calcium, phosphorus, magnesium, zinc, manganese, copper, selenium, sodium, potassium, chloride, iron and selenium. The compositions can also be supplemented with: chromium, molybdenum, iodine, taurine, carnitine and choline may also require supplementation.

The osmolality of standardized human milk formulations featured herein can affect adsorption, absorption, and digestion of the compositions. High osmolality, e.g., above about 400 mOsm/Kg $H_2O$, has been associated with increased rates of NEC, a gastrointestinal disease that affects neonates (see, e.g., Srinivasan et al., Arch. Dis. Child Fetal Neonatal Ed. 89:514-17, 2004). The osmolality of the human milk compositions of the disclosure is typically less than about 400 mOsm/Kg $H_2O$. The osmolality can be adjusted by methods known in the art.

Methods of Making Human Milk Compositions

The human milk compositions described herein are produced from whole human milk. The human milk may be obtained from an infant's own mother or from one or more donors. In certain embodiments, the human milk is pooled to provide a pool of human milk. For example, a pool of human milk comprises milk from two or more (e.g., ten or more) donors. As another example, a pool of human milk comprises two or more donations from one donor.

Obtaining Human Milk from Qualified and Selected Donors

Generally, human milk is provided by donors, and the donors are pre-screened and approved before any milk is processed. Various techniques are used to identify and qualify suitable donors. A potential donor must obtain a release from her physician and her child's pediatrician as part of the approval process. This helps to insure, inter alia, that the donor is not chronically ill and that her child will not suffer as a result of the donation(s). Methods and systems for qualifying and monitoring milk collection and distribution are described, e.g., in U.S. Pat. Nos. 8,545,920; 7,943,315; 9,149,052; 7,914,822 and 8,278,046, which are incorporated herein by reference in its entirety. Donors may or may not be compensated for their donation.

Usually, donor screening includes a comprehensive lifestyle and medical history questionnaire that includes an evaluation of prescription and non-prescription medications, testing for drugs of abuse, and testing for certain pathogens. The donor or her milk may be screened for, e.g., human immunodeficiency virus Type 1 (HIV-1), HIV-2, human T-lymphotropic virus Type 1 (HTLV-I), HTLV-II, hepatitis B virus (HBV), hepatitis C virus (HCV), and syphilis. These examples are not meant to be an exhaustive list of possible pathogens to be screened for.

Donors may be periodically requalified. A donor who does not requalify or fails qualification is deferred until such time as they do, or permanently deferred if warranted by the results of requalification screening. In the event of the latter situation, all remaining milk provided by that donor is removed from inventory and destroyed or used for research purposes only.

A donor may donate at a designated facility (e.g., a milk bank office) or, in a preferred embodiment, express milk at home. If the donor will be expressing milk at home, she will measure the temperature in her freezer with, e.g., a supplied thermometer to confirm that it is cold enough to store human milk in order to be approved.

Testing Donor Identity

Once the donor has been approved, donor identity matching may be performed on donated human milk because the milk may be expressed by a donor at her home and not collected at a milk banking facility. In a particular embodiment, each donor's milk can be sampled for genetic markers, e.g., DNA markers, to guarantee that the milk is truly from the approved donor. Such subject identification techniques are known in the art (see, e.g., U.S. Pat. No. 7,943,315, which is incorporated herein by reference in its entirety). The milk may be stored (e.g., at −20° C. or colder) and quarantined until the test results are received.

For example, the methods featured herein may include a step for obtaining a biological reference sample from a potential human breast milk donor. Such sample may be obtained by methods known in the art such as, but not limited to, a cheek swab sample of cells, or a drawn blood sample, milk, saliva, hair roots, or other convenient tissue. Samples of reference donor nucleic acids (e.g., genomic DNA) can be isolated from any convenient biological sample including, but not limited to, milk, saliva, buccal cells, hair roots, blood, and any other suitable cell or tissue sample with intact interphase nuclei or metaphase cells. The sample is labeled with a unique reference number. The sample can be analyzed at or around the time of obtaining the sample for one or more markers that can identify the potential donor. Results of the analysis can be stored, e.g., on a computer-readable medium. Alternatively, or in addition, the sample can be stored and analyzed for identifying markers at a later time.

It is contemplated that the biological reference sample may be DNA typed by methods known in the art such as STR analysis of STR loci, HLA analysis of HLA loci or multiple gene analysis of individual genes/alleles. The DNA-type profile of the reference sample is recorded and stored, e.g., on a computer-readable medium.

It is further contemplated that the biological reference sample may be tested for self-antigens using antibodies known in the art or other methods to determine a self-antigen profile. The antigen (or another peptide) profile can be recorded and stored, e.g., on a computer-readable medium.

A test sample of human milk is taken for identification of one or more identity markers. The sample of the donated human milk is analyzed for the same marker or markers as the donor's reference sample. The marker profiles of the reference biological sample and of the donated milk are compared. The match between the markers (and lack of any additional unmatched markers) would indicate that the donated milk comes from the same individual as the one who donated the reference sample. Lack of a match (or presence of additional unmatched markers) would indicate that the donated milk either comes from a non-tested donor or has been contaminated with fluid from a non-tested donor.

The donated human milk sample and the donated reference biological sample can be tested for more than one marker. For example, each sample can be tested for multiple DNA markers and/or peptide markers. Both samples, however, need to be tested for at least some of the same markers in order to compare the markers from each sample.

Thus, the reference sample and the donated human milk sample may be tested for the presence of differing identity marker profiles. If there are no identity marker profiles other than the identity marker profile from the expected subject, it generally indicates that there was no fluid (e.g., milk) from other humans or animals contaminating the donated human milk. If there are signals other than the expected signal for that subject, the results are indicative of contamination. Such contamination will result in the milk failing the testing.

The testing of the reference sample and of the donated human milk can be carried out at the donation facility and/or milk processing facility. The results of the reference sample tests can be stored and compared against any future donations by the same donor.

Screening for Contaminants and Adulterants

The milk is also tested for pathogens. The milk is genetically screened, e.g., by polymerase chain reaction (PCR), to identify, e.g., viruses, such as HIV-1, HBV and HCV. A microorganism panel that screens for various bacterial species, fungus and mold via culture may also be used to detect contaminants. For example, a microorganism panel may test for aerobic count, *Bacillius cereus, Escherichia coli, Salmonella, Pseudomonas*, coliforms, *Staphylococcus aureus*, yeast and mold. In particular, *B. cereus* is a pathogenic bacterium that cannot be removed through pasteurization. Pathogen screening may be performed both before and after pasteurization.

In addition to screening for pathogens, the donor milk may also be tested for drugs of abuse (e.g., cocaine, opiates, synthetic opioids (e.g. oxycodone/oxymorphone) methamphetamines, benzodiazepine, amphetamines, and THC) and/or adulterants such as non-human proteins. For example, an ELISA may be used to test the milk for a non-human protein, such as bovine proteins, to ensure, e.g., that cow milk or cow milk infant formula has not been added to the human milk, for example to increase donation volume when donors are compensated for donations.

Adulterants include any non-human milk fluid or filler that is added to a human milk donation, thereby causing the donation to no longer be unadulterated, pure human milk. Particular adulterants to be screened for include non-human milk and infant formula. As used herein, "non-human milk" refers to animal-, plant- and synthetically-derived milks. Examples of non-human animal milk include, but are not limited to, buffalo milk, camel milk, cow milk, donkey milk, goat milk, horse milk, reindeer milk, sheep milk, and yak milk. Examples of non-human plant-derived milk include, but are not limited to, almond milk, coconut milk, hemp milk, oat milk, rice milk, and soy milk. Examples of infant formula include, cow milk formula, soy formula, hydrolysate formula (e.g., partially hydrolyzed formula or extensively hydrolyzed formula), and amino acid or elemental formula. Cow milk formula may also be referred to as dairy-based formula. In particular embodiments, the adulterants that are screened for include cow milk, cow milk formula, goat milk, soy milk, and soy formula.

Methods known in the art may be adapted to detect non-human milk proteins, e.g., cow milk and soy proteins, in a human milk sample. In particular, immunoassays that utilize antibodies specific for a protein found in an adulterant that is not found in human milk can be used to detect the presence of the protein in a human milk sample. For example, an enzyme-linked immunosorbent assay (ELISA), such as a sandwich ELISA, may be used to detect the presence of an adulterant in a human milk sample. An ELISA may be performed manually or be automated. Another common protein detection assay is a western blot, or immunoblot. Flow cytometry is another immunoassay technique that may be used to detect an adulterant in a human milk sample. ELISA, western blot, and flow cytometry protocols are well known in the art and related kits are commercially available. Another useful method to detect adulterants in human milk is infrared spectroscopy and in particular mid-range Fourier transform infrared spectrometry (FTIR).

The human milk may be pooled prior to screening. In one embodiment, the human milk is pooled from more than one donation from the same individual. In another embodiment, the human milk is pooled from two or more, three or more, four or more, five or more, six or more, seven or more, eight or more, nine or more, or ten or more individuals. In a particular embodiment, the human milk is pooled from ten or more individuals. The human milk may be pooled prior to obtaining a sample by mixing human milk from two or more individuals. Alternatively, human milk samples may be pooled after they have been obtained, thereby keeping the remainder of each donation separate.

The screening step will yield a positive result if the adulterant is present in the human milk sample at about 20% or more, about 15% or more, about 10% or more, about 5% or more, about 4% or more, about 3% or more, about 2% or more, about 1% or more, or about 0.5% or more of the total volume of the milk donation.

The screening of the donated human milk for one or more adulterants can be carried out at the donation facility and/or milk processing facility.

Human milk that has been determined to be free of an adulterant, or was found to be negative for the adulterant, is selected and may be stored and/or further processed. Human milk that contains an adulterant will be discarded and the donor may be disqualified. For example, if an adulterant is found in two or more human milk samples from the same donor, the donor is disqualified. In another embodiment, if an adulterant is found in one or more human milk samples from the same donor, the donor is disqualified.

Processing Human Milk

Once the human milk has been screened, it is processed to produce a high fat product, e.g., a human cream composition. The donation facility and milk processing facility can be the same or different facility. Processing of milk can be carried out with large volumes of human milk, e.g., about 75 liters/lot to about 10,000 liters/lot of starting material (e.g. about 2,500 liters/lot or about 2,700 liters/lot or about 3,000 liters/lot or about 5,000 liters/lot or about 7,000 liters/lot, about 7,500 liters/lot or about 10,000 liters/lot).

Methods of obtaining compositions that include lipids from human milk to provide nutrition to patients are described in U.S. Pat. No. 8,377,445 filed on May 17, 2010 (National Stage Entry of PCT/US07/86973 filed on Dec. 10, 2007), the contents of which are incorporated herein in their entirety.

After the human milk is carefully analyzed for both identification purposes and to avoid contamination as described above, the milk can optionally undergo filtering, e.g., through about a 200 micron filter, and the further optional step of heat treatment. For example, the composition can be treated at about 63° C. or greater for about 30 minutes or more. Next, the milk is transferred to a separator, e.g., a centrifuge, to separate the cream (i.e., the fat portion) from the skim. The skim can be transferred into a second processing tank where it remains at about 2 to 8° C. until a filtration step. Optionally, the cream separated from the skim, can undergo separation again to remove more skim.

Following the separation of cream and skim, the skim portion undergoes further filtration, e.g., ultrafiltration. This process concentrates the nutrients in the skim milk by filtering out the water. The water obtained during the concentration is referred to as the permeate. The resulting skim portion can be further processed to produce human milk fortifiers and/or standardized human milk formulations.

Processing of human milk to obtain human milk fortifiers (e.g., PROLACTPLUS™ Human Milk Fortifiers, e.g., PROLACT+4®, PROLACT+6®, PROLACT+8®, and/or PROLACT+10®, which are produced from human milk and contain various concentrations of nutritional components) and the compositions of the fortifiers are described in U.S. Pat. No. 8,545,920, filed on Nov. 29, 2007, the contents of which are incorporated herein in their entirety. These fortifiers can be added to the milk of a nursing mother to enhance the nutritional content of the milk for, e.g., a preterm infant.

Methods of obtaining standardized human milk formulations (exemplified by PROLACT20™, and/or PROLACT24™) and formulations themselves are also discussed in U.S. Pat. No. 8,545,920, filed on Nov. 29, 2007, the contents of which are incorporated herein in their entirety. These standardized human milk formulations can be used to feed, e.g., infants. They provide a nutritional human-derived formulation and can substitute for mother's milk.

Use of Human Milk Compositions

The disclosed human milk compositions are particularly useful for providing nutrition for subjects who are undergoing or have undergone surgery in order to provide enough calories to meet the increased nutritional requirements associated with conditioning regimen before surgery, the complications resulting from the surgery procedure and the demands of physical growth of subjects. The compositions of the present invention are useful in situations where infants and/or children require enteral feeding. Feeding TPN is often used to feed subjects who have undergone surgery. However, due to the negative effects associated with TPN, enteral feeding is desired. Enteral feeding can also be combined with TPN. The use of human lipids for parenteral nutrition, a practice of intravenous feeding (e.g., total parenteral nutrition), for a patient in need thereof is described in U.S. Pat. Nos. 8,821,878 and 8,377,445 the contents of each of which are incorporated herein in their entirety.

Compositions and methods of the present disclosure are useful in providing nutrition to infants prior to surgery, after surgery, or before and after surgery.

Feeding guidelines prior to surgery may include providing human milk compositions of the present invention at 2.5 ml/kg every three hours for a total of 20 ml/kg per day. If tolerating well, may advance feeds per cue with a maximum volume as per standard practice at the center, for example feeds may be advanced by 20 ml/kg per day every 24 hours for a maximum determined by the attending physician, for example the maximum feed may be 60 ml/kg per day.

Feeding guidelines post-surgery may include a phased approach. Phase 1 may comprise initiation of trophic feeds with human milk compositions of the present invention when ready as per attending physician at 1 ml per kg body weigh per day with a goal of 1 to 5 days. Phase 1 may also include the initiation of feeds at 20 ml/kg/day with continued advancements after 24 hours by 20 to 40 ml/kg/day. Phase 2 may comprise advancing to a goal of about 60 to about 100 ml/kg/day. Feeding advancements may occur every 6-12 hours with progress to full feeds in Phase 2. Phase 3 may begin once phase 2 has been tolerated for 24 hours. Phase 3 may comprise advancing 10 to 20 ml/kg to a goal of about 130 to about 140 ml/kg/day. Advancement to phase 4 may occur after tolerance in phase 3 has been observed for a minimum of 24 hours. Stepwise fortification may occur during each phase beginning at 24 cal/oz in phase 2, advancing to 26 calories/oz in Step 3 to 28 calories/oz in step 4 and finally 30 calories/oz at the completion of Step 4. If poor weight gain is demonstrated, additional advances of 10 to 20 ml/kg/day may be utilized and titrated to weight gain. One of skill in the art will understand that the above represents an exemplary protocol and that the exact timing of calorie and/or volume increases will depend on the post-surgical situation that is encountered (e.g. gastroschisis vs cardiac) or the subject being fed (e.g. a preterm infant vs a term infant vs an older infant vs an adult).

All patents, patent applications, and references cited herein are incorporated in their entireties by reference. Unless defined otherwise, technical and scientific terms used herein have the same meaning as that commonly understood by one of skill in the art.

EXAMPLES

The following examples are intended to illustrate but not limit the disclosure.

Example 1

Standardized Human Milk and Fortifier Products

In order to provide a nutritional supplement that can add the desired amounts of calories to mother's own or donor milk without adding a significant amount of volume, a human cream composition was produced that can be delivered enterally, thereby avoiding the negative effects associated with TPN. Human milk from previously screened and approved donors was mixed together to generate a pool of donor milk. In a clean room environment, the pool of donor milk was further tested for specific pathogens and bovine proteins. Specifically, PCR testing was used to screen for the presence of HIV-1, HBV, and HCV in the milk. A microbiological panel was also performed that tests for, e.g., aerobic count, *Bacillius cereus, Escherichia coli, Salmonella, Pseudomonas,* coliforms, *Staphylococcus aureus,* yeast and mold.

FIG. 1 is a chart showing an embodiment of generating a human milk fortifier. The screened, pooled milk undergoes filtering, e.g., through about a 200 micron filter (step 2), and heat treatment (step 3). For example, the composition can be treated at about 63° C. or greater for about 30 minutes or more. Depending on the methods used, however, the initial filtering and/or heat treatment step may be omitted. In step 4, the milk is transferred to a separator, e.g., a centrifuge, to separate the cream from the skim. The skim can be transferred into a second processing tank where it remains at about 2 to 8° C. until a filtration step (step 5).

Optionally, the cream separated from the skim in step 4, can undergo separation again to yield more skim.

Following separation of cream and skim (step 4), a desired amount of cream is added to the skim, and the composition undergoes further filtration (step 5), e.g., ultrafiltration. This process concentrates the nutrients in the skim milk by filtering out the water. The water obtained during the concentration is referred to as the permeate. Filters used during the ultrafiltration can be postwashed and the resulting solution added to the skim to maximize the amount of nutrients obtained. The skim is then blended with the cream (step 6) and samples taken for analysis. At this point during the process, the composition generally contains: about 8.5% to 9.5% of fat; about 3.5% to about 4.3% of protein; and about 8% to 10.5% of carbohydrates, e.g., lactose.

After the separation of cream and skim in step 4, the cream flows into a holding tank, e.g., a stainless steel container. The cream can be analyzed for its caloric, protein and fat content. When the nutritional content of cream is known, a portion of the cream can be added to the skim milk that has undergone filtration, e.g., ultrafiltration, (step 5) to achieve the caloric, protein and fat content required for the specific product being made. Minerals can be added to the milk prior to pasteurization.

At this point, the processed composition can be frozen prior to the addition of minerals and thawed at a later point for further processing. Any extra cream that was not used can also be stored, e.g., frozen. Optionally, before the processed composition is frozen, samples are taken for mineral analysis. Once the mineral content of the processed milk is known, the composition can be thawed (if it were frozen) and a desired amount of minerals can be added to achieve target values.

After step 6 and/or the optional freezing and/or mineral addition, the composition undergoes pasteurization (step 7). For example, the composition can be placed in a process tank that is connected to the high-temperature, short-time (HTST) pasteurizer via platinum-cured silastic tubing. After pasteurization, the milk can be collected into a second process tank and cooled. Other methods of pasteurization known in the art can be used. For example, in vat pasteurization the milk in the tank is heated to a minimum of 63° C. and held at that temperature for a minimum of thirty minutes. The air above the milk is steam heated to at least three degrees Celsius above the milk temperature. In one embodiment, the product temperature is about 66° C. or greater, the air temperature above the product is about 69° C. or greater, and the product is pasteurized for about 30 minutes or longer. In another embodiment, both HTST and vat pasteurization are performed.

The resulting fortifier composition is generally processed aseptically. After cooling to about 2 to 8° C., the product is filled into containers of desired volumes, and various samples of the fortifier are taken for nutritional and bioburden analysis. The nutritional analysis ensures proper content of the composition. A label that reflects the nutritional analysis is generated for each container. The bioburden analysis tests for presence of contaminants, e.g., total aerobic count, *B. cereus, E. coli, Coliform, Pseudomonas, Salmonella, Staphylococcus*, yeast, and/or mold. Bioburden testing can be genetic testing.

The product is packaged and shipped once the analysis is complete and desired results are obtained.

Example 2

Use Of Human Milk Products For Infants Undergoing Surgery

A randomized controlled trial is undertaken to evaluate growth velocity and clinical outcomes of infants with single ventricle physiology fed an exclusive human milk diet with early nutritional fortification following surgical repair. While the methods and clinical protocol described herein are done on a 7 day old or younger term infant, a person of skill in the art would understand that the compositions and methods would be suitable for older children, adults and pre-term infants.

In the United States, about 40,000 births per year are associated with a congenitally malformed heart. Infants with single ventricle physiology (~15% of all CHD) face a significant challenge in terms of growth both short and long term, particularly after the first palliative surgery during the inter-stage (Anderson J B, Iyer S B, Schidlow D N et al. Variation in Growth of infants with single ventricle. J Pediatrics 2012;161:16-21).

Currently, the standard of care is to feed these infants with unfortified human milk or formula until infant is almost at full feeds. Early feeding of fortified human milk has been shown to improve growth in a neonatal population at highest risk for growth failure such as preterm infants, (Cristofalo E A, Schanler R J, Blanco C L, et al. Randomized trial of exclusive human milk versus preterm diets in extremely premature infants. J Pediatrics, doi: 10.1016/j.jpeds.2013.07.011, 2013. Hair A B, Hawthorne K M, Chetta K E, Abrams S A. Human milk feeding supports adequate growth in infants ≤1250 grams birth weight. BMC Res Notes, 2013, 6:459. Doi: 10.1186/1756-0500-6-459.) In addition, it has been well-demonstrated over the past few years that extremely premature infants (<1250 g birthweight) fed a 100% human milk diet demonstrate significantly better clinical outcomes, e.g. decreased incidence of NEC and time spent on intravenous feedings (TPN), than babies fed a diet containing any cow milk-based components. Currently, all participating centers do not utilize an exclusive human milk diet in term infants with a single ventricle physiology heart defect as they need increased caloric intake via fortification utilizing cow's milk derived products (fortifiers/formula). While their growth patterns are similar when a standard nutritional protocol is used, a much more aggressive protocol is possible with a 100% human milk diet resulting in improved growth at similar nutritional volumes (Hair, 2013).

In this single blinded (physician investigator), randomized, controlled trial we evaluate growth velocity and clinical outcomes in infants with single ventricle physiology fed an exclusive human milk diet during their initial hospitalization after birth and through the 30 days post-surgical repair feeding period or hospital discharge, whichever comes first.

The study population comprises infants less than or equal to 7 days old with single ventricle cardiac physiology whose enteral nutrition, if any, consists of an exclusive human milk diet prior study enrollment and who require surgical palliation within the first 1 month of life.

Subjects are randomized to one of two groups (described in more detail below) at birth or immediately following diagnosis if prenatal care was not obtained prior to birth. Parents who decline participation by their infants in the study are asked to consent to data gathering on their infants who will be treated and fed per institutional practice. The data on these individuals is summarized and evaluated descriptively in comparison with the actual trial results. Any infant who is randomized and has undergone cardiac repair will continue on the intervention even if exclusion criteria are later discovered (i.e. microarray comes back positive for 22q11 deletion). Infants are terminated from study if is not in the best interest of the infant (i.e. chylothorax, NEC)

All patients receive exclusive maternal human milk or donor human milk prior to randomization. Once randomized, patients in Group One receive an exclusive human milk diet prior to the surgery and throughout the 30 day feeding period following surgical repair or until hospital discharge, whichever comes first. Day 1 is defined as the day of the first enteral feed post-surgery. Patients in Group Two (Control Group) receive maternal human milk or formula or donor human milk (per standard of care at each hospital) in the pre-surgical period. During the post-surgical period, the control group receives human milk or formula, as per feeding algorithm.

The primary objective is to evaluate growth velocity (weight velocity [g/kg/day] and weight z-score from WHO growth charts) at 30 days after the initiation of feed post-surgery for infants with single ventricle physiology who are fed an exclusive human milk diet from birth throughout the 30 day feeding period following surgical repair or until hospital discharge, whichever comes first. Day 1 is defined as the day of the first enteral feed post-surgery.

The secondary objectives are to evaluate the role of an exclusive human milk diet with regards to secondary measures of growth such as the rate of linear growth (cm/week and z-score from WHO growth charts) and incremental rate of head circumference growth (cm/week and z-score from WHO growth charts) over the duration of the initial 6 months of the post-surgical period or prior to the $2^{nd}$ stage palliation surgery whichever came first. Additional secondary measures include 1) Feeding intolerance defined as nil per os (NPO) for at least 24 hours in the 30 days of post-surgery enteral feeding period (day 1 is the first day of feeding post-op). NPO due to elective surgeries or procedures will not be defined as feeding intolerance 2) Post-operative length of stay in the hospital and length of stay in the intensive care/cardiac unit 3) Incidence of key morbidities in the 30 day post-surgical period, such as:

Confirmed sepsis (defined as clinical signs and symptoms consistent with sepsis in association with the isolation of a causative organism from a culture of blood. A definitive demonstration of infection must include one or more of the following: 1) positive blood cultures (in cases of Coagulase-negative Staphylococcus [CoNS] at least two positive cultures separated temporally and physically are required.) 2) positive urine cultures 3) positive CSF cultures. For the purposes of this endpoint only culture-proven sepsis will be evaluated in the analyses. The number of cultures taken for each patient will be recorded to collect data in regards of number of events of "suspected sepsis" vs "confirmed sepsis".

Necrotizing enterocolitis (NEC), defined as stage II or greater per Bell's criteria and whether surgical intervention was required Wound infections defined as per CDC Surgical Site infection: Infection that occurs within 30 days after any operative procedure and involves only skin and subcutaneous tissue of the incision and has at least one of the following: a) purulent drainage; b) organisms identified from an aseptically-obtained specimen from the superficial incision or subcutaneous tissue by a culture or non-culture based microbiologic testing methods which is performed for purposes of clinical diagnosis or treatment (not surveillance); c) superficial incision that is deliberately opened by a surgeon/attending physician and patient has at least one of the following signs or symptoms: pain or tenderness, localized swelling, erythema, or heat; d) diagnosis of a superficial incisional SSI by the surgeon or attending physician. Cellulitis, stitch abscess alone or localized pin site infection does not qualify. Classify as deep if it involves deep soft tissues (fascia and muscle layers).

Wound dehiscence that requires intervention (wound vac)

Days of parenteral nutrition (PN) in the 30 day post-surgical period

Developmental outcome are evaluated based on Bayley III score at 18-24 months.

Data regarding cardiac anatomy and physiology risk factors, as assessed by routine echocardiography, are periodically collected throughout the study period from preoperative period to 18 to 24 months evaluation (ideally at pre-first surgery, at pre-$2^{nd}$ stage palliation surgery, within 1 week post-surgery if obtained as standard of care, and at 18-24 months). This included data regarding: congenital heart anatomic subtype, qualitative assessment of dominant ventricular function, qualitative assessment of AV valve regurgitation, degree of systemic outflow obstruction (aortic stenosis or coarctation) degree of aortic insufficiency, and presence of residual pulmonary venous obstruction.

Quality objectives included length of time on human milk diet post-discharge at the 3, 6 and 18-24 month follow up visits.

Supportive variables included time from birth to surgical repair, need for cardiac re-operation, need for interventional cardiac catheterization, data collection of any non-cardiac surgery and extracorporeal membrane oxygenation (ECMO), and major STS morbidities/complications (Jacobs M L, O'Brien S M, et al. An empirically based tool for analyzing morbidity associated with operations for congenital heart disease. J Thorac. Cardiovasc. Surg. 2013; 145: 1046-1057) Major STS morbidities/complications as defined by local STS database managers include complete heart block (CHB) requiring pacemaker (PM), diaphragm paralysis requiring plication, tracheostomy at discharge, renal failure requiring dialysis, new post-operative neurological deficit persisting at discharge, need for post-op mechanical circulatory support, unplanned re-operation.

In addition, once a week a sample of the human milk (4 ml of breast or donor thawed to prepare the feeding for the day before any fortification is added) being fed are tested for macronutrient content (calories, protein, carbohydrates and fat). The frequency of direct breastfeeding per day are recorded during the study intervention. The length of time the patient is fed breastmilk is recorded at the follow up visits.

As a result of earlier fortification and better feeding tolerance, the infants have improved growth and wound healing; in addition to the immunological and anti-inflammatory benefits of an exclusive human milk diet, complications that occur post-surgical repair are reduced. The overall length of stay in the hospital and the associated cost of extended hospitalization are decreased. Furthermore, there is lower incidence of confirmed sepsis and other morbidities such as NEC.

Feeding Management PRE-surgery

1. Readiness to feed is determined by the clinician team. Criteria to consider to initiate enteral feeds in an attempt to standardize between centers include 1) Hemodynamically stable (stable vital signs per attending physician), reasonable urine output (>2 ml/kg/hour) and good perfusion by exam 2) Minimal or no acidosis, based on stable lactate levels or base deficit 3) Receiving no or low vasoactive support for at least 12 hours, May be on milrinone and either dopamine ≤3 mcg/kg/min or epinephrine ≤0.03 mcg/kg/min. OK if receiving prostaglandin (PGE 1), and OK if UAC or UVC in place. The Wernovsky inotrope score will be calculated for information purposes (Wernovsky et al., 1995). Not following these criteria is NOT considered a violation of protocol.

2. Initiate PO feeds (20 ml/kg/day) if tolerating well may advance PO feeds per cues with a maximum volume as per standard practice at the center.

3. If not engaged in PO feeds but meets above criteria: May keep NPO OR START TROPHIC FEEDS at (20 ml/kg/day) via OG, NG or NJ.

4. TYPE OF FEEDING AFTER RANDOMIZATION: If infant is in Group 1 (Study group), infant will receive maternal human milk or donor human milk. If infant is in Group 2 infant will receive human milk (maternal or donor) or formula (Any term formula 20 cal/oz) as per standard of care at each hospital. Research coordinator, dietitian and dietary techs will be unblinded to group allocation. All treating clinicians to include: attending physicians, residents, fellows, RN's, APN's will remain blinded to group allocation.

Criteria for NOT feeding pre-surgery include 1) Feeding difficulties or other intestinal disease such as dysmotility as determined by treating physicians which may include increase in abdominal girth, emesis, paucity of bowel sounds, no stool for >48 hours with a history of regular stooling, increased gastric residuals if NG feeding as per standard practice at the hospital (Infants with NEC or intestinal surgical intervention are excluded from study) and 2) Infant with history of pre-operative shock and/or multi-organ failure (diagnosed with at least 2 of the following active diagnoses: Acute tubular necrosis, acute liver failure with coagulopathy, intestinal bleeding). Clinician to determine if pre-operative shock and multi-organ failure is severe enough to not feed.

Feeding Management Post-surgery

1. Readiness to feed is determined by the clinician team. Criteria to consider to initiate enteral feeds in an attempt to standardize between centers include 1) Hemodynamically stable (stable vital signs per attending physician), reasonable urine output (>2 ml/kg/hour) and good perfusion by exam, 2) Minimal or no acidosis, based on stable lactate levels or base deficit and 3) Receiving no or low vasoactive support for at least 12 hours, May be on milrinone and either dopamine ≤3 mcg/kg/min or epinephrine ≤0.03 mcg/kg/min. OK if receiving prostaglandin (PGE 1), and OK if UAC or UVC in place. The Wernovsky inotrope score will be calculated for information purposes (Wernovsky et al., 1995). Not following these criteria is NOT considered a violation of protocol.

Figure 2:
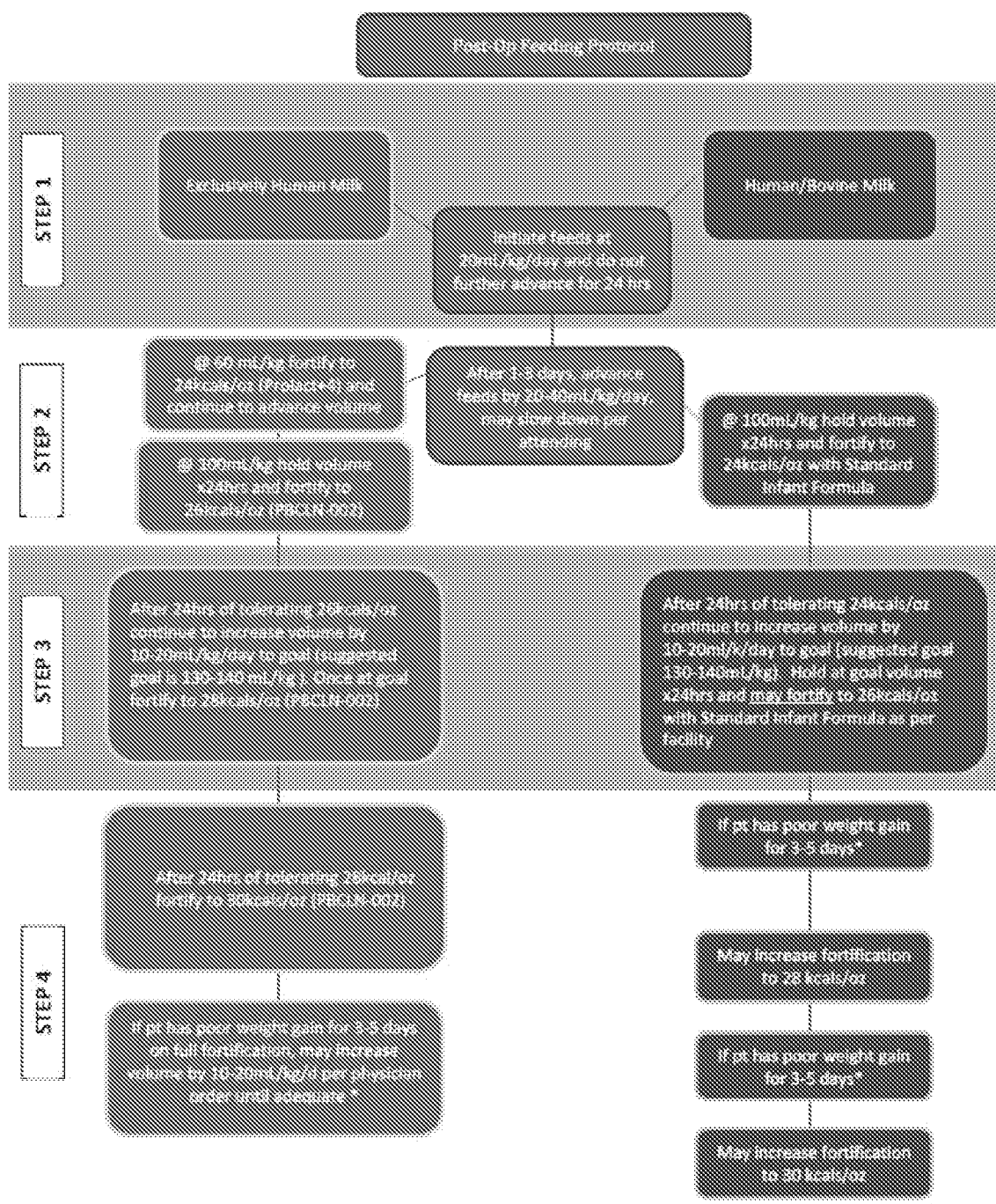
FIG. 2 is a flowchart of an exemplary post-op feeding protocol.

2. Follow Post-surgical feeding algorithm (FIG. 2) for feeding volume, type, fortification and advancement. In brief, fortification will be initiated at 60 ml/kg/day in the exclusive human milk group; the control group will initiate fortification as per ordinary care at the participating institution in the post-surgical period (expected to be at 100 ml/kg/day).

Figure 3:
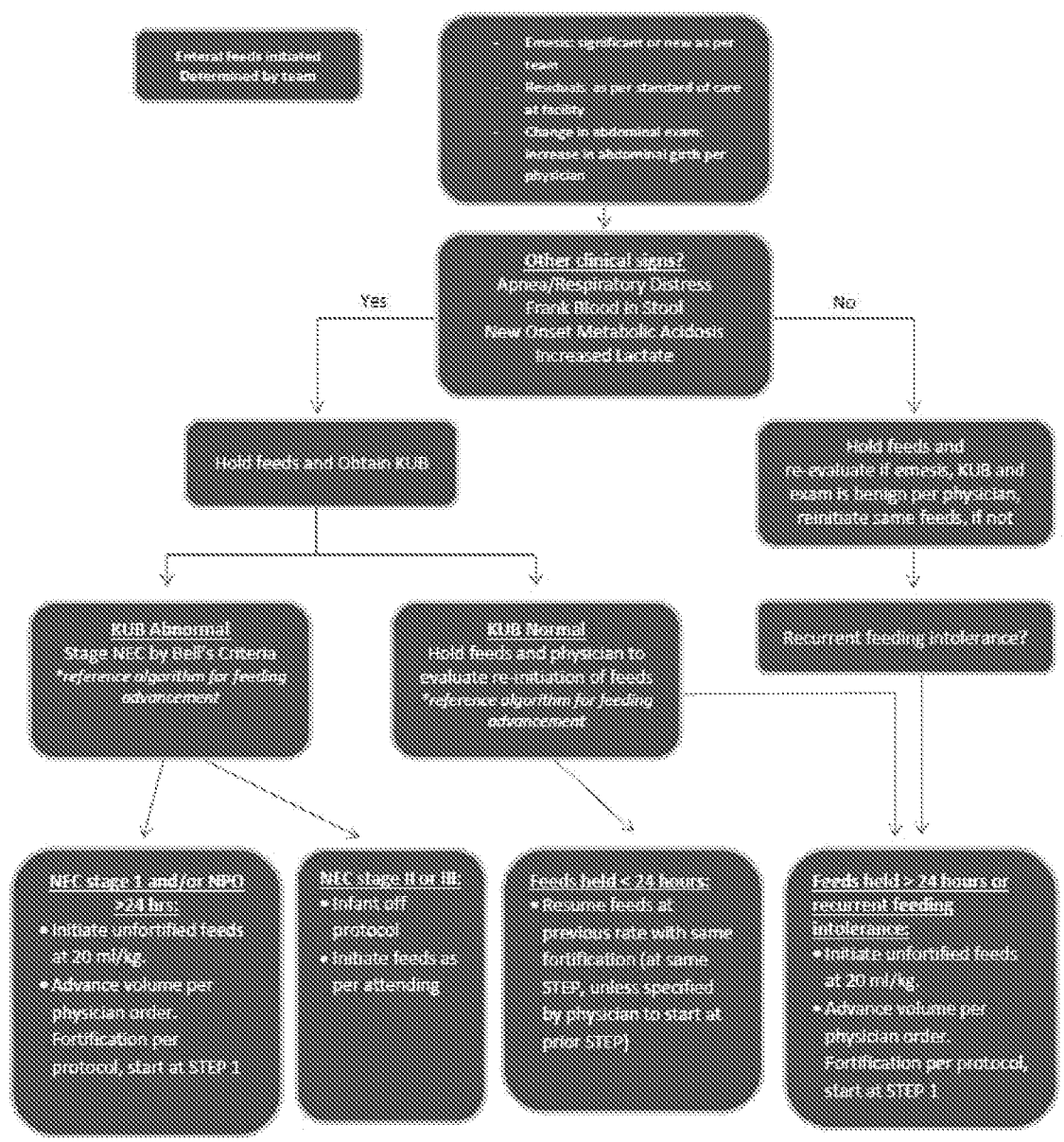
FIG. 3 is a flowchart of the feeding intolerance algorithm.

3. Suggest following feeding intolerance algorithm for holding/advancing feeds (FIG. 3). Feeds can be held at the discretion of physician, not following algorithm is NOT considered a deviation of protocol.

Criteria for NOT feeding post-surgery include 1) Feeding difficulties or other intestinal disease such as dysmotility as determined by treating physicians including increase in abdominal girth, emesis, paucity of bowel sounds, no stool for >48 hours with a history of regular stooling, increased gastric residuals if NG feeding as per standard practice at the hospital (Infants with NEC or intestinal surgical intervention are excluded from study), 2) Infant with history of pre-operative shock and/or multi-organ failure (diagnosed with at least 2 of the following active diagnoses: Acute tubular necrosis, acute liver failure with coagulopathy, intestinal bleeding). Clinician to determine if pre-operative shock and multi-organ failure is severe enough to not feed and 3) Presence of chylothorax. If developed while on study, infant will be off protocol.

Type of feeding and fortification at a certain volume is protocol driven. The specific post-op nutritional protocol is given in one year, more than one year, more than two years, more than three years, more than four years, more than five years, and any duration longer than five years. In particular embodiments of any of the methods described herein, a treatment regimen comprises a subject being provided with the halogen compound, e.g., iodide, over a period of a lifetime. Clinicians determine enteral volume, frequency to be given to infant per day and route (PO/NG/NJ). The order should read: type of feeding and fortification as per protocol. Otherwise this study will not alter the medical and/or surgical management of patients with single ventricle physiology.

Figure 4:
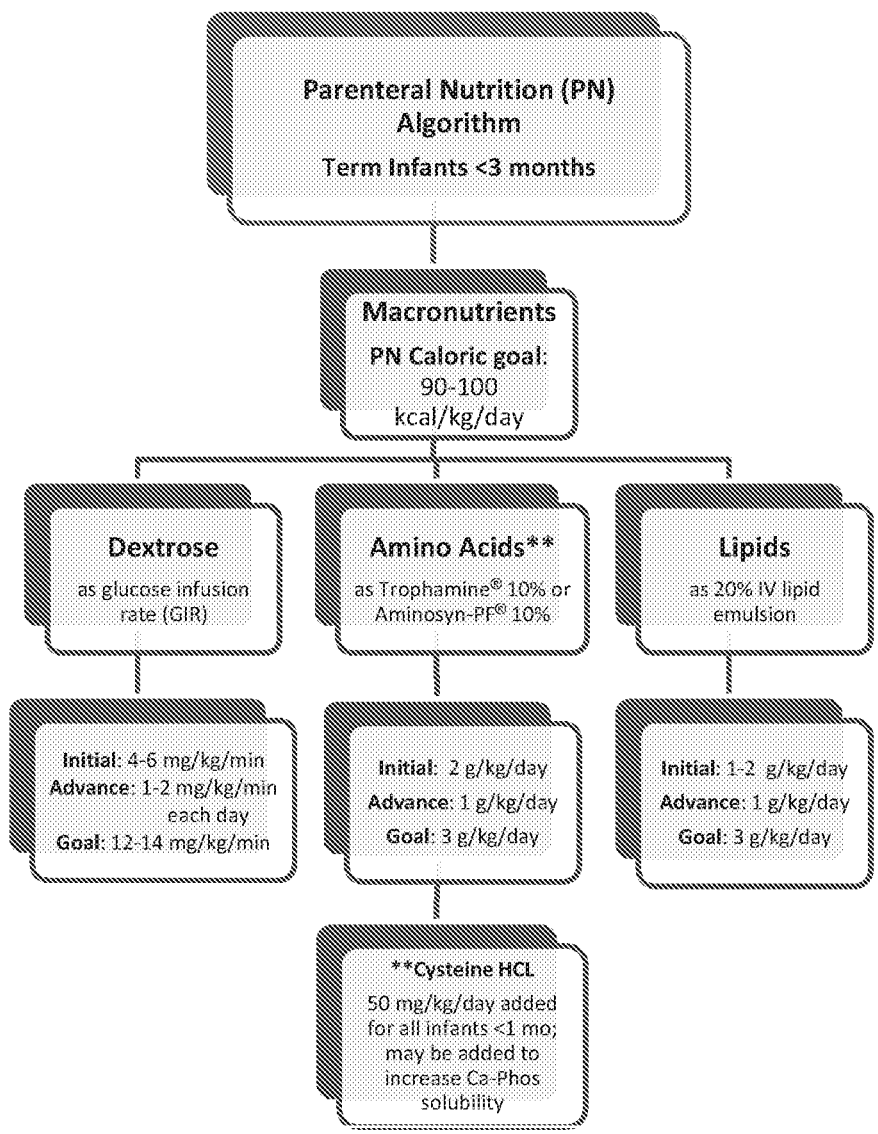
FIG. 4 is a flowchart of the parenteral nutrition algorithm.

In both the investigational and control groups, TPN is given in both the pre-surgical and immediate post-surgical period as needed according to the attending physicians (see FIG. 4 for suggested TPN algorithm). The amount of TPN given each day will be recorded in terms of volume, kcal and protein. This overall randomization process will be performed within each of the study centers.

Randomization between the study groups will be performed using a permuted block randomization scheme (with the block size remaining blinded to study investigators). A predetermined randomization table will be provided to each study site by the study statistician and this will be given to an individual at each site not responsible for patient evaluation. Randomization will take place as soon as the infant is enrolled in the study. Study allocation will be disclosed to research coordinator, dietitians, and dietary techs in order to follow feeding algorithm and ensure appropriate fortification and type of milk is provided to each patient. All treating clinicians to include: attending physicians, residents, fellows, RN's, APN's will remain blinded to group allocation but the stage of fortification will be disclosed upon request (stage as defined in post-op feeding algorithm, FIG. 2).

Infants remain on this feeding algorithm for 30 days or until discharge, whichever comes first. Once discharge is being anticipated, transitioning off donor human milk and fortifier will begin and will follow the weaning table (FIG. 5). Once an infant is completely off Human Based Milk Fortifier (Prolacta Product), formula/HMF will be added to provide a minimum of 24 kcal/oz per the individual site's practice fortification can be adjusted as per attending physician. For the control group (study arm 1) transition to a discharge formula will not occur as they are already receiving formula/HMF. Once an infant is off intervention, fortification can be adjusted as per the attending physician.

Transition to discharge feeding regimen is summarized in FIG. 5 and is only needed for infants strictly on human milk arm. If anticipating discharge within 5 days begin transition off DBM (donor breast milk) following feeding chart below. Optionally, transition day 3 may be skipped. If EBM (expressed breast milk) is available transition to EBM fortified to 24 kcal/oz with term formula. If standard of care is to discharge on donor human milk at that facility then it can be used. If no EBM is available transition to TERM formula fortified to 24 kcal/oz. TERM Formula to be used can be chosen per facility by Dietitian or Cardiac team, Minimum concentration of 20 cal/oz during intervention period. Direct breast feeding may be incorporated into feeding regimen per facility.

Example 3

Statistical Analysis

Quantitative data are summarized using mean±standard deviation and/or median±interquartile range, and qualitative data will be summarized using proportions and percentages.

The primary endpoints of the study include weight velocity (g/kg/day) in the 30 day enteral feeding period following surgical repair or until hospital discharge, whichever comes first, as well as length (cm/week) and head circumference growth (cm/week) in the first 6 months post-surgery (or prior to the $2^{nd}$ palliation surgery).

The experimental and control groups will be compared using the Wilcoxon rank-sum test in each case. The calculation of weight velocity in g/kg/day will be based on the method proposed by Patel et al. (2009). Calculation of length and head circumference velocity will be based on the change in the measurements from the initial reading to the last value obtained in the relevant time period divided by the time frame in weeks.

The incidences of any feeding intolerance, confirmed sepsis, NEC, wound infection and wound dehiscence will be compared between the study groups using the Fisher's exact test. While these analyses look only at whether or not these outcomes occurred, if there are multiple occurrences, the rates will be evaluated using the two-sample exact test of Poisson rates (based on the algorithm found in the program StatXact 11).

The length of stay in the hospital, length of stay in the intensive care/cardiac unit and days of parenteral nutrition in the post-surgical period will be compared using the Wilcoxon rank-sum test. However, if there is any censoring (e.g. if the infant is transferred or dies) in either of these variables, the data will be evaluated using the Kaplan-Meier estimation scheme and compared with the log rank test.

Multivariate regression models (linear for quantitative variables, Cox proportional hazards for censored data, logistic for qualitative data, and Poisson for count data) may be used in a secondary adjusted analysis to account for predefined relevant covariates (i.e. birth weight, gender, type of surgical procedure, etc.). In all analyses, significance will be declared for any p-value less than 0.05 with no adjustment for multiple endpoints.

For developmental outcomes, the Bayley scores at 18-24 months will be compared using the Wilcoxon rank sum test.

For exploratory objectives, various quantitative measures obtained from the echo cardiography are evaluated using the Wilcoxon rank-sum test and categorical outcomes will be compared between the groups using either the Fisher's exact test (dichotomous data) or the chi-square test for homogeneity using an exact calculation of the p-value (StatXact 11) for multichotomous outcomes.

For quality objectives, length of time on an exclusive human milk diet post-discharge at the 3 and 6 month (+/−2 weeks) and the 18-24 month follow up visits are individually evaluated by the Wilcoxon rank-sum test. However, if the information is not completely known at a specific time, then the log rank test will be used because of censoring.

For supportive variables, the time from birth to surgical repair will be analyzed using the Wilcoxon rank-sum test. The need for re-operation will be compared between the groups using Fisher's exact test.

What is claimed is:

1. A method for providing nutrition to a subject who is about to undergo or has undergone surgery for a congenital heart defect, the method comprising enterally or orally administering to said subject a fortified human milk composition comprising a human milk fortifier mixed with human milk,
    wherein the human milk fortifier comprises a human protein constituent from about 35 mg/mL to about 45 mg/mL and a human fat constituent from about 80 mg/mL to about 100 mg/mL;
    and
    wherein the subject is a full-term infant born with a congenital heart defect.

2. The method of claim 1, wherein administering the fortified human milk composition improves growth velocity including rate of weight gain, incremental linear growth, and/or incremental rate of head circumference growth, relative to administration of non-human milk based formula.

3. The method of claim 1, wherein administering the fortified human milk composition reduces incidence of feeding intolerance, sepsis, and/or necrotizing enterocolitis (NEC), relative to administration of non-human milk based formula.

4. The method of claim 1, wherein the subject is 7 days old or younger.

5. The method of claim 1, wherein the congenital heart defect is single ventricle physiology.

6. The method of claim 1, wherein the human milk is mother's own milk.

7. The method of claim 1, wherein the human milk is donor milk.

8. The method of claim 1, wherein the human milk comprises about 20 kcal/ounce.

9. The method of claim 1, wherein the fortified human milk composition comprises a ratio of the human milk fortifier to the human milk from 30:70 to 50:50.

10. The method of claim 1, wherein the fortified human milk composition comprises a human protein constituent from about 10 to about 30 mg/ml protein, a human fat constituent from about 40 to about 70 mg/ml fat, and a human carbohydrate constituent from about 80 to about 100 mg/ml carbohydrate.

11. The method of claim 1, wherein the subject is administered the human milk composition for at least 30 days after the surgery.

12. The method of claim 11, wherein the subject is fed an exclusive human milk diet for the at least 30 days after the surgery.

13. A method for providing nutrition to a subject who is about to undergo or has undergone surgery for a congenital heart defect, the method comprising enterally or orally administering to said subject a fortified human milk composition comprising a human milk fortifier mixed with human milk,
    wherein the human milk fortifier comprises a human protein constituent from about 35 mg/mL to about 45 mg/mL and a human fat constituent from about 80 mg/mL to about 100 mg/mL;
    wherein the fortified human milk composition comprises a ratio of the human milk fortifier to the human milk from 30:70 to 50:50;
    wherein the fortified human milk composition comprises a human protein constituent from about 10 to about 30 mg/ml protein and a human fat constituent from about 40 to about 70 mg/ml fat; and
    wherein the subject is a full-term infant born with a congenital heart defect.

* * * * *